United States Patent
Wu et al.

(10) Patent No.: US 10,140,705 B2
(45) Date of Patent: *Nov. 27, 2018

(54) DRAWER VISION SYSTEM

(71) Applicant: Siemens Healthcare Diagnostics Inc., Tarrytown, NY (US)

(72) Inventors: Wen Wu, Kirkland, WA (US); Yao-Jen Chang, Princeton, NJ (US); David Liu, Franklin Park, NJ (US); Benjamin Pollack, Jersey City, NJ (US); Terrence Chen, Princeton, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/317,497

(22) PCT Filed: Jun. 10, 2015

(86) PCT No.: PCT/US2015/035092
§ 371 (c)(1),
(2) Date: Dec. 9, 2016

(87) PCT Pub. No.: WO2015/191702
PCT Pub. Date: Dec. 17, 2015

(65) Prior Publication Data
US 2017/0124704 A1    May 4, 2017

Related U.S. Application Data

(60) Provisional application No. 62/010,370, filed on Jun. 10, 2014.

(51) Int. Cl.
*G06T 7/00* (2017.01)
*G05B 21/00* (2006.01)
(Continued)

(52) U.S. Cl.
CPC .............. *G06T 7/0012* (2013.01); *G01C 11/06* (2013.01); *G01N 21/952* (2013.01); *G05B 21/00* (2013.01);
(Continued)

(58) Field of Classification Search
CPC ......... G01N 1/312; G01N 2035/00089; G01N 35/00584; G01N 21/952; G01N 35/02;
(Continued)

(56) References Cited

U.S. PATENT DOCUMENTS

2004/0115796 A1    6/2004   Burns
2005/0130220 A1*   6/2005   Lemmo ............... B01J 19/0046
                                                                 435/6.11
(Continued)

FOREIGN PATENT DOCUMENTS

WO    2010/036808 A1    4/2010

OTHER PUBLICATIONS

Extended EP Search Report dated May 23, 2017 of corresponding European Application No. 15806102.8, 4 Pages.
(Continued)

*Primary Examiner* — Jingge Wu

(57) ABSTRACT

Methods and systems for detecting properties of sample tubes in a laboratory environment include a drawer vision system that can be trained and calibrated. Images of a tube tray captured by at least one camera are analyzed to extract image patches that allow a processor to automatically determine if a tube slot is occupied, if the tube has a cap, and if the tube has a tube top cup. The processor can be trained using a random forest technique and a plurality of training image patches. Cameras can be calibrated using a three-dimensional calibration target that can be inserted into the drawer.

20 Claims, 15 Drawing Sheets

(51) Int. Cl.
*G01N 21/952* (2006.01)
*G01C 11/06* (2006.01)
*G06K 9/62* (2006.01)
*G06T 7/80* (2017.01)
*G05B 21/02* (2006.01)

(52) U.S. Cl.
CPC .......... G05B 21/02 (2013.01); G06K 9/6282 (2013.01); G06T 7/0008 (2013.01); G06T 7/80 (2017.01); *G06T 2207/20081* (2013.01); *G06T 2207/30024* (2013.01); *G06T 2207/30072* (2013.01); *G06T 2207/30204* (2013.01)

(58) Field of Classification Search
CPC ......... G06T 7/0012; G06T 2207/30072; G06T 7/0004; G06T 7/0008; G06T 7/80; G06K 9/4604; G06K 9/6267; G06K 9/6282; G01C 11/06
See application file for complete search history.

(56) References Cited

U.S. PATENT DOCUMENTS

| | | | | |
|---|---|---|---|---|
| 2005/0169733 | A1* | 8/2005 | Drynkin | B25J 9/026 414/404 |
| 2006/0000296 | A1* | 1/2006 | Salter | B01L 9/06 73/863.01 |
| 2006/0178578 | A1* | 8/2006 | Tribble | B65B 3/003 600/432 |
| 2008/0056958 | A1 | 3/2008 | Vijay et al. | |
| 2009/0154764 | A1* | 6/2009 | Khan | B65B 3/003 382/100 |
| 2009/0324032 | A1 | 12/2009 | Chen | |
| 2010/0254589 | A1 | 10/2010 | Gallagher | |
| 2012/0236306 | A1 | 9/2012 | Ostermeyer | |
| 2013/0019697 | A1 | 1/2013 | McKeen et al. | |
| 2014/0112558 | A1 | 4/2014 | Bean et al. | |
| 2016/0011221 | A1* | 1/2016 | Hegedus | G01N 1/312 435/286.3 |
| 2016/0025757 | A1* | 1/2016 | Pollack | G01N 21/253 348/143 |
| 2016/0109406 | A1* | 4/2016 | Boeke | G01N 27/44782 506/39 |

OTHER PUBLICATIONS

Anonymous: "Product Catalog—Hardy diagnostics online Ordering", May 10, 2017 (May 10, 2017), XP055371736, Retrieved from the Internet: URL:https://catalog.hardydiagnostics.com/cp_prod/product/5504g-nesting-cups-polystyrene-for-13mm-tubes-1ml-1000-per-case-by-globe-scientific-labware-plastic-cups-tubes-caps-vials [retrieve on May 11, 2017] *the whole document*.

PCT International Search Report and Written Opinion dated Sep. 1, 2015 (8 pages).

* cited by examiner

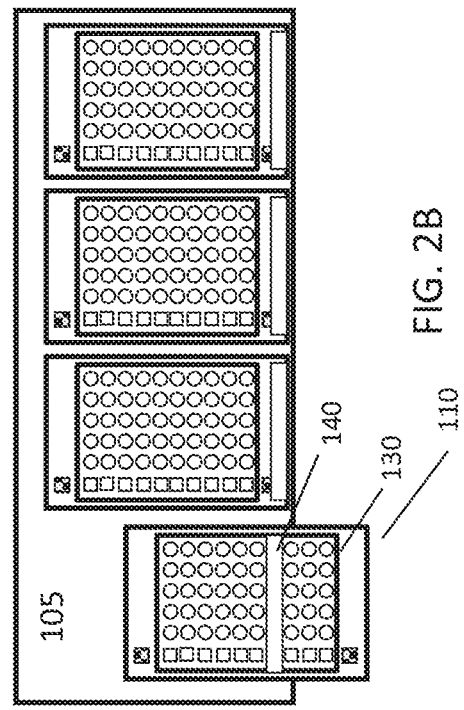
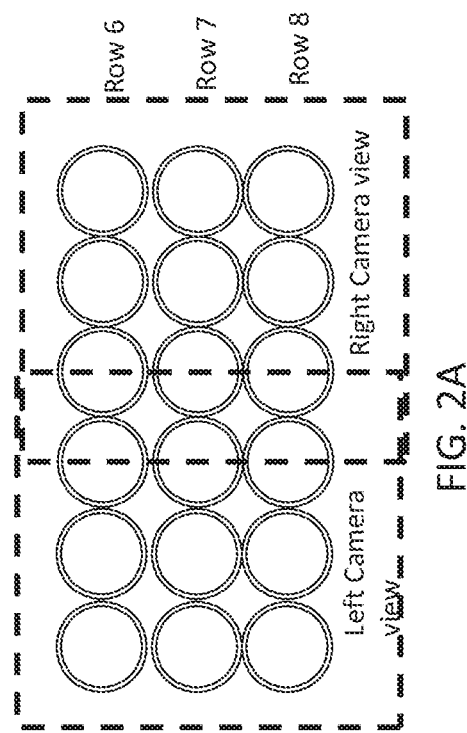
FIG. 2B
FIG. 2A

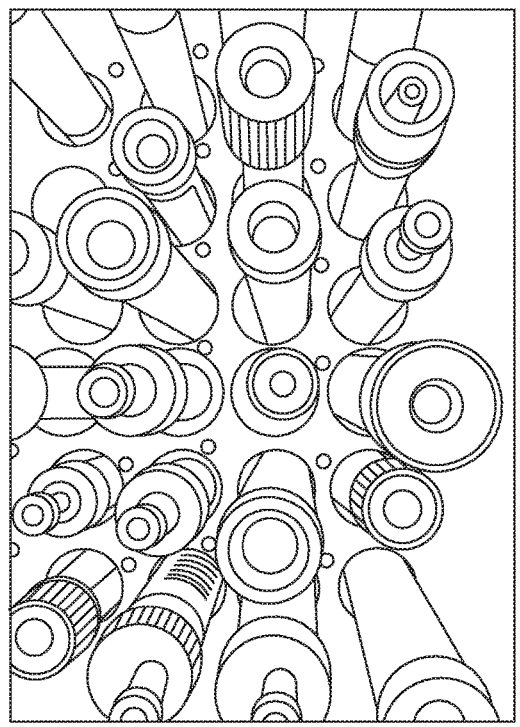
610
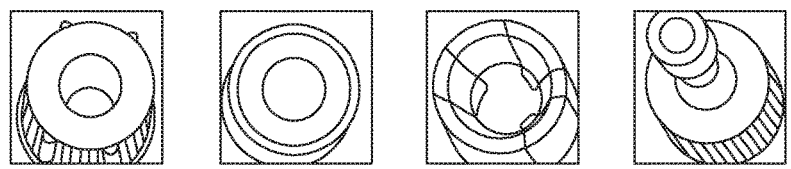
612
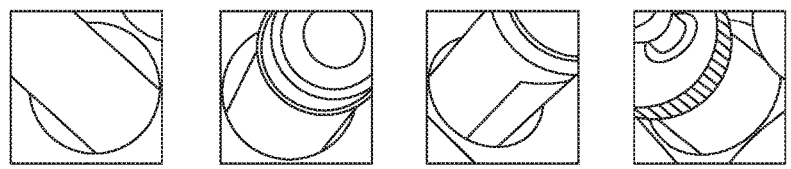
614
FIG. 6

DRAWER VISION SYSTEM

This application claims priority to U.S. provisional application Ser. No. 62/010,370 filed Jun. 10, 2014, which is incorporated herein by reference in its entirety.

TECHNOLOGY FIELD

The present invention relates generally to characterizing tubes contained in a tube tray, and more particularly to training and calibrating systems for capturing images of a tube tray to determine characteristics of the tubes held within the tray.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) into which tubes or vials containing patient samples have been loaded. Because of the variety of assays needed in a modern IVD lab, and the volume of testing necessary to operate a lab, multiple analyzers are often employed in a single lab. Between and amongst analyzers, automation systems may also be used. Samples may be transported from a doctor's office to a lab, stored in the lab, placed into an automation system or analyzer, and stored for subsequent testing.

Storage and transport between analyzers is typically done using trays. A tray is typically an array of several patient samples stored in test tubes. These trays are often stackable and facilitate easy carrying of multiple samples from one part of the laboratory to another. For example, a laboratory may receive a tray of patient samples for testing from a hospital or clinic. That tray of patient samples can be stored in refrigerators in the laboratory. Trays of patient samples can also be stored in drawers. In some automation systems, an analyzer can accept a tray of patient samples and handle the samples accordingly, while some analyzers may require that samples be removed from trays by the operator and placed into carriers (such as pucks) before further handling. Trays are generally passive devices that allow samples to be carried and, in some cases, arranged in an ordered relationship.

Generally, information about sample tubes stored in a tray is not known until an operator or sample handling mechanism interacts with each tube. For example, a sample handling robot arm may pick up a tube, remove it from the tray and place it into a carrier. The carrier can then travel to a decapper station to remove any possible cap and pass by a barcode reader so that a barcode on the side of the tube can be read to reveal the contents of the tube. In many prior art sample handling mechanisms, the identity of the tube is not known until after the tube is removed from the tray. In this manner, all tubes in a tray will often be handled the same way until after a tube is placed onto a carrier in an automation system.

Some systems allow an operator to insert a tray into a drawer and automatically rotate tubes to assist in later evaluation and identification. However, such systems still rely on conventional automation systems to move sample tubes from trays to barcode reading stations and little or no characterization of sample tubes is performed until after the tube is removed from the tube tray. This can result in practical constraints on the variety of tubes used, because a sample handler cannot account for a great degree of variance in height, width, shape, and whether caps or tube top cups are placed on the tubes.

Accordingly, most prior art tube tray drawers and workflow lacks intelligent systems to automatically characterize tubes in a tube tray when placed into an instrument, instead relying on post-loading processing of tubes once they are removed from the tube tray or more manual characterization in the workflow.

SUMMARY

It is desirable to ascertain various pieces of information relating to a tray, the tubes, and the tubes' location within the tray, such as, for example, the tray slots containing a tube; a tube's center point, diameter, and height; the tray's orientation within a drawer; whether a tube is covered with a cap or tube-top cup. It is desirable to obtain these and other pieces of information quickly, without expensive equipment, and without handling or touching the tubes. Accordingly, it is further desirable to have an efficient training and calibration scheme for the cameras and image processing used by a drawer vision system (DVS) that can accomplish these above goals.

Embodiments of the present invention address the above needs by providing a characterization of tube trays by capturing images of the trays and related calibration and training schemes.

According to an embodiment, a method for detecting properties of sample tubes, includes steps of receiving a series of images of a tray from at least one camera, extracting a plurality of image patches from each image, and automatically determining, using a processor, from a first subset of the plurality image patches, each patch corresponding to one of a plurality of slots in the tray, whether each of a plurality of slots contains a sample tube. For those plurality of slots that contain a sample tube, the processor automatically determines, from a second subset of the plurality image patches, each patch corresponding to the top of the sample tube, whether each sample tube has a cap. For those tubes that do not have a cap, the processor automatically determines, from the second subset of the plurality image patches whether each sample tube has a tube-top cup or is a plain tube.

According to one aspect of some embodiments, the series of images comprises images of the tray at predetermined positions in a tray drawer. In some embodiments, a set of fiducial markers on the tray surface is used to determine each patch corresponding to one of a plurality of slots in the tray. According to one aspect of some embodiments, the step of automatically determining whether each of a plurality of slots contains a sample tube includes a. identifying a patch in at least one image in the series of images that corresponds to that slot for each slot, and determining, for each identified patch, a probability that the slot is occupied by a sample tube.

According to one aspect of some embodiments, the step of automatically determining whether each sample tube has a cap includes identifying a patch in at least one image in the series of images that corresponds to the top of the sample tube for each sample tube, and determining, for each identified patch, a probability that the sample tube has a cap. According to one aspect of some embodiments, the step of automatically determining whether each sample tube has a tube-top cup includes identifying a patch in at least one image in the series of images that corresponds to the top of the sample tube for each sample tube, and determining, for each identified patch, a probability that the sample tube has a tube-top cup.

According to one aspect of some embodiments, the processor determines for each sample tube, at least one of: tube type; tube height, tube diameter; tube offset; cap color; and fluid type. According to one aspect of some embodiments, the processor automatically identifies a tray type from the series of images.

According to one aspect of some embodiments, a processor calibrates at least one camera, which is configured to capture the plurality of images, using a 3D target having a plurality of unique digital markers. According to one aspect of some embodiments, software trains the processor to perform the determining steps using a random forest technique and a plurality of training images.

According to one embodiment, a vision system for use in an in vitro diagnostics environments includes a drawer configured to receive a tray, which includes a plurality of slots, each configured to receive a sample tube, and at least one camera configured to capture a series of images of the tray as the drawer is moved. A processor is configured to perform steps of receiving the series of images of the tray from the camera; extracting a plurality of image patches from each image; automatically determining, from a first subset of the plurality image patches, each patch corresponding to one of a plurality of slots in the tray, whether each of a plurality of slots contains a sample tube; automatically determining, from a second subset of the plurality image patches, each patch corresponding to the top of the sample tube, whether each sample tube has a cap for those plurality of slots that contain a sample tube; and for those tubes that do not have a cap, automatically determining, from the second subset of the plurality image patches whether each sample tube has a tube-top cup.

According to one aspect of some embodiments, the series of images includes images of the tray at predetermined positions in the drawer. According to one aspect of some embodiments, a set of fiducial markers on the surface of the tray is used to determine each patch corresponding to one of a plurality of slots in the tray. According to one aspect of some embodiments, in determining whether each of a plurality of slots contains a sample tube, the processor identifies a patch in at least one image in the series of images, which corresponds to that slot for each slot and determines a probability that the slot is occupied by a sample tube for each identified patch.

According to one aspect of some embodiments, in determining whether each sample tube has a cap, the processor identifies a patch in at least one image in the series of images that corresponds to the top of the sample tube for each sample tube and determines a probability that the sample tube has a cap, for each identified patch. According to one aspect of some embodiments, in automatically determining whether each sample tube has a tube-top cup, the processor identifies a patch in at least one image in the series of images that corresponds to the top of the sample tube, for each sample tube and determines a probability that the sample tube has a tube-top cup, for each identified patch.

According to one aspect of some embodiments, the processor is further configured to automatically determine, for each sample tube, at least one of a tube type, a tube height, a tube diameter, a tube offset, a cap color, and a fluid type. According to one aspect of some embodiments, the processor is configured to perform the step of automatically identifying a tray type from the series of images. According to one aspect of some embodiments, the processor is configured to perform the step of calibrating the at least one camera using a 3D target having a plurality of unique digital markers. According to one aspect of some embodiments, the processor is configured to perform the step of training the processor to perform the determining steps using a random forest technique and a plurality of training images.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 2A-2F provide illustrations of a work envelope as exemplary images are captured for a row of tubes, according to an embodiment;

FIG. 6 is a photographic view of sample images and image patches for use with some embodiments;

DETAILED DESCRIPTION OF ILLUSTRATIVE EMBODIMENTS

Figure 1:
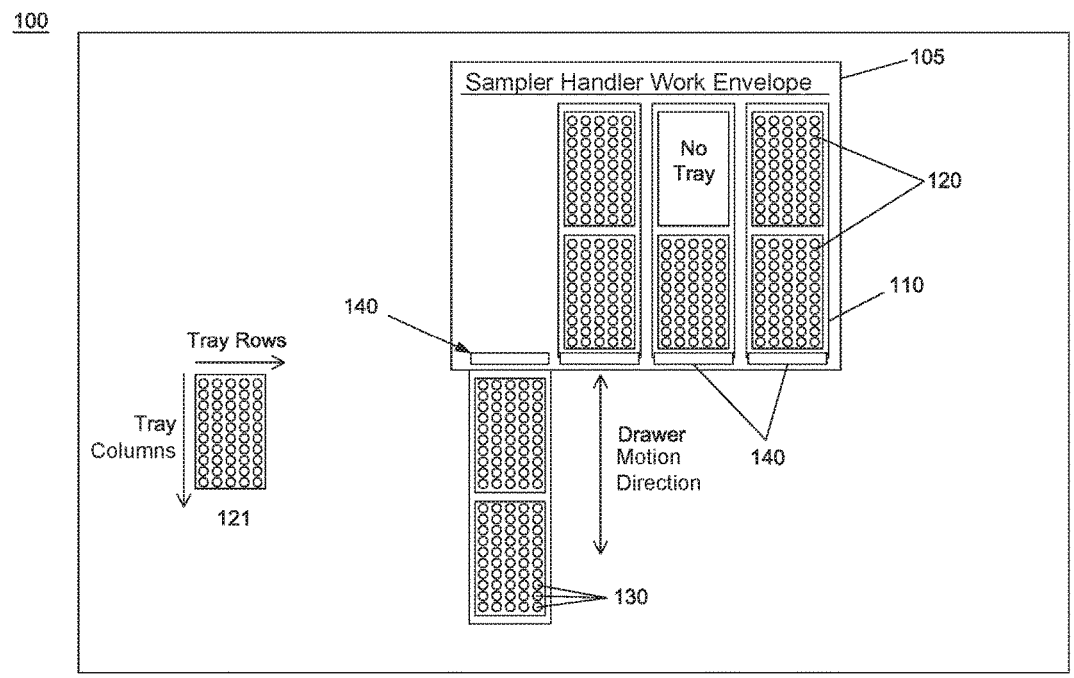
FIG. 1 is a representation of a system for characterizing through image analysis tube trays and tubes held in a drawer, according to an embodiment.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Carriers/Trays/Racks: A carrier may be distinguishable from a tray, which may commonly refer to a device that does not travel along an automation track (e.g., carried by an operator) and is configured to hold a plurality of payloads (e.g., sample tubes). A rack is a general term to describe a device that is configured to hold a plurality of payloads (e.g., sample tubes). A rack may refer to a tray (when used outside an automation track) or carrier (when configured to traverse an automation track) that is configured to carry a plurality of payloads. Racks may refer to one-dimensional or two-dimensional arrays of slots, in some embodiments.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Processor: A processor may refer to one or more processors and/or related software and processing circuits. This may include single or multicore processors, systems, or distributed processing architectures, as appropriate, for implementing the recited processing function in each embodiment.

Tubes/sample vessels/fluid containers: Samples may be carried in vessels, such as test tubes or other suitable vessels, to allow carriers to transport samples without contaminating the carrier surfaces.

Exemplary Embodiments

Embodiments of the present invention relate to capturing images of a tube tray configured to fit within a drawer and hold a plurality of tubes in slots that are arranged in an array of rows and columns and more particularly to training and calibrating systems for this task. Images captured by cameras viewing a tube tray are used to characterize the tray, as well as the tubes held on the tray. In particular, according to embodiments, by analyzing the images, various features of the tubes can be determined, such as, for example, the height, diameter, and center point of the tubes, whether the tubes have a cap or tube-top cup, the barcodes on top surfaces of the tubes (e.g., on a cap) or on a tray, and identifying the tray slots containing a tube. Other features of sample tubes that may be determined via these images are discussed throughout. This information is valuable in an IVD environment in which a sample handler is processing the tubes and moving the tubes to analyzers for testing and analysis. Embodiments of the present invention are particularly well suited for, but in no way limited to, IVD environments.

An exemplary system for use with methods disclosed herein is the drawer vision system discussed in co-owned PCT Application No.: PCT/US14/27217, which is incorporated, herein by reference, in its entirety. FIG. 1 is a representation of a system 100 in which tube trays 120 and tubes 130 contained thereon are characterized by obtaining and analyzing images thereof, according to an embodiment. One or more drawers 110 are movable between an open and a closed position and are provided in a work envelope 105 for a sample handler. One or more tube trays 120 may be loaded into a drawer 110 or may be a permanent feature of the drawer 110. Each tube tray 120 has an array of rows and columns of slots (as depicted in exemplary tray 121) in which tubes 130 may be held.

According to some embodiments of an imaging system that can be used with the concepts disclosed herein, images are taken of a tube tray 120; the images are analyzed to determine characteristics of the tube tray 120 and the tubes 130. A moving-tray/fixed camera approach is used, according to embodiments provided herein, to capture the images for analysis thereof. As the tube tray 120 is moved into the work envelope 105 by, for example, manually or automatically pushing in the drawer 110, an image capture system 140 is used to take images of the tube tray 120 and the tubes 130 contained thereon. According to an embodiment, the image capture system 140 includes one or more cameras positioned at or near the entrance to the work envelope 105. The one or more cameras may be positioned above the surface of the tube tray 120. For example, the cameras may be placed three to six inches above the surface to capture a high resolution image of the tube tray 120. Other distances and/or positioning may also be used depending on the features of the cameras and the desired perspective and image quality. Optionally, the image capture system 140 may include one or more lighting sources, such as an LED flash. As the tube tray 120 is already required to be slid into the work envelope 105, adding the fixed image capture system 140 does not add an excess of cost or complexity to the work envelope 105. The image capture system 140 also includes one or more processors to perform the image capture algorithms, as further described below.

According to an embodiment, the image capture system 140 captures an image each time a row of the tube tray 120 is moved into a center position or a position substantially centered under the one or more cameras. More than one row of the tubes 130 can be captured in this image, with one row being centered or substantially centered beneath the image capture system 140, while adjacent rows are captured from an oblique angle in the same image. By capturing more than one row at a time, the rows of tubes 130 are captured from multiple perspectives, providing for depth and perspective information to be captured in the images for each tube 130.

According to an embodiment, a tri-scopic perspective of a row of tubes 130 is captured as the row of tubes 130 are captured in multiple images. For example, a single row may appear in the bottom portion of an image (from an oblique perspective) when the preceding row is centered or substantially centered beneath the image capture system 140; that single row may then appear substantially centered in an image (from a substantially top-down perspective) when the row of tubes itself is centered or substantially centered beneath the image capture system 140; and that single row may appear in the top portion of an image (from another oblique perspective) and when the subsequent row of tubes is centered or substantially centered beneath the image capture system 140. In another embodiment, a stereoscopic perspective of a row of tubes may be captured as images are taken when the image capture system 140 is centered or substantially centered above a point between two adjacent rows (allowing each row to appear in two images at two oblique perspectives). Similarly, rows may appear in more than three images, in more than three perspectives, allowing more three-dimensional information about each tube to be gleaned from a plurality of images. The invention is not limited to tri-scopic and stereoscopic perspectives of the row of tubes 130; instead, depending on features of the cameras and the positioning of the image capture system 140 with respect to the work envelope 105, additional perspectives may be obtained.

Figure 2C:
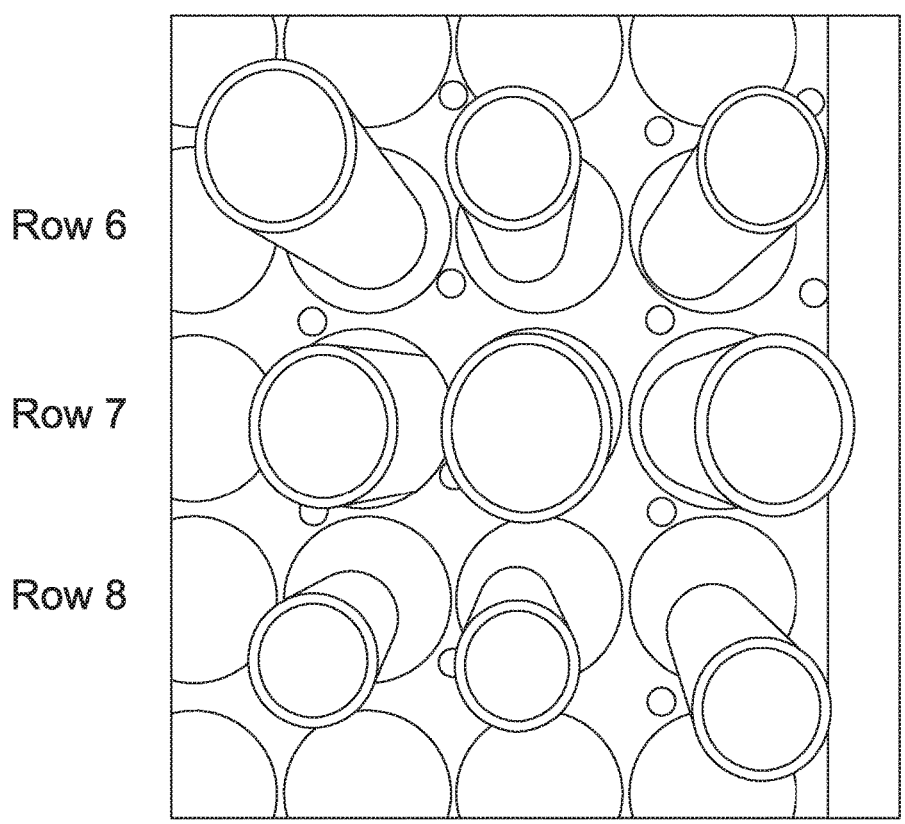
Figure 2E:
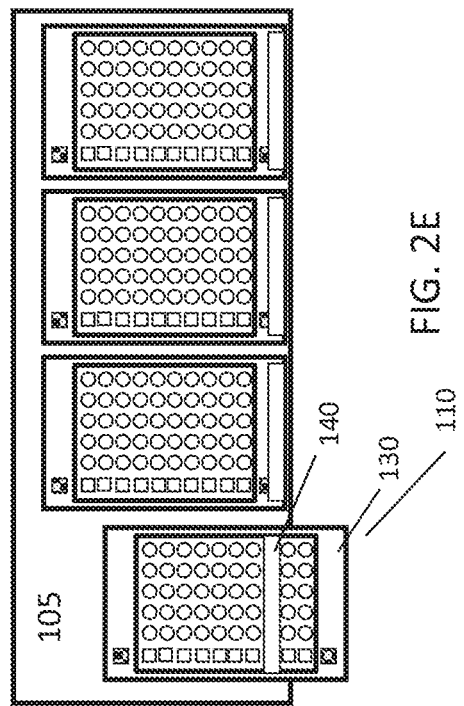
Figure 2D:
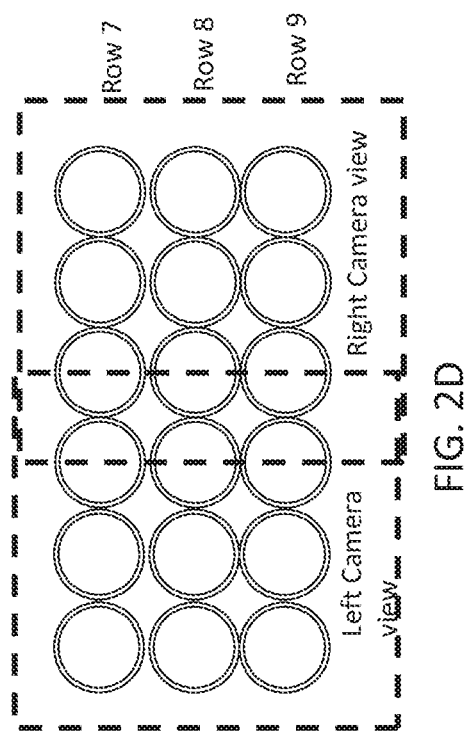
Figure 2F:
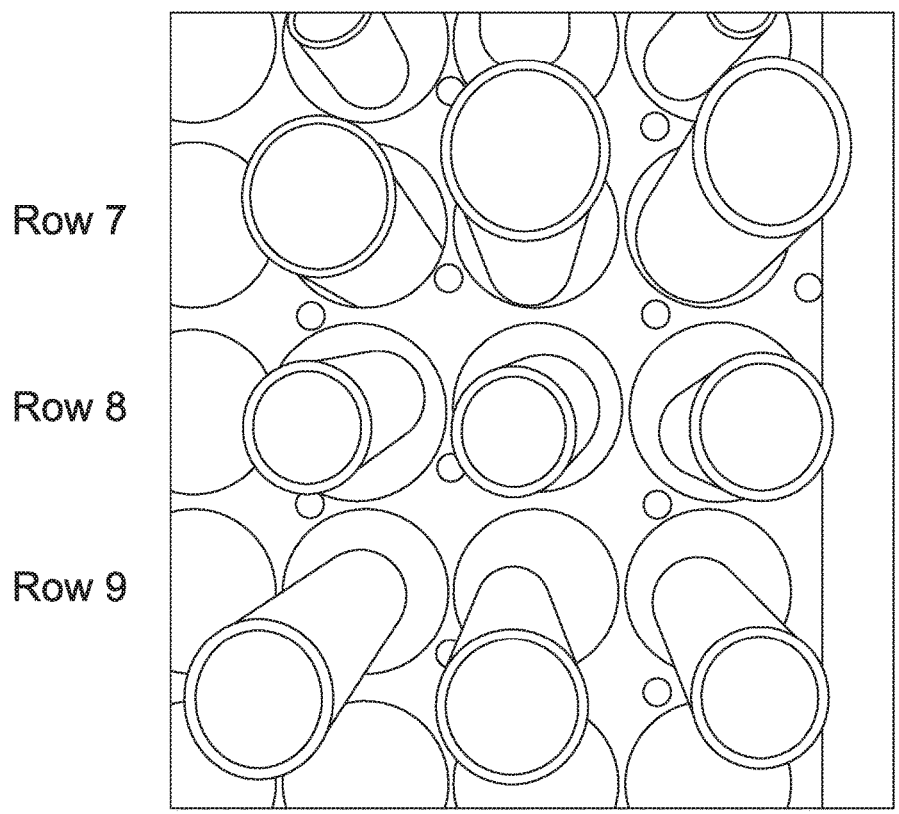

FIGS. 2A-2F provide illustrations of the work envelope 105 as exemplary images are captured for a row of tubes 130. The image capture system 140 captures multiple perspectives of the row of the tubes 130 as the row is advanced into the work envelope 105. As shown in FIGS. 2A-2C, an image of row 10, is captured directly or near directly under the one or more cameras as row 10 is moving into the work envelope 105 (i.e., the drawer 110 is being slid into the work envelope 105), allowing row 10 to appear substantially in the center of the image (e.g., as shown in FIG. 2C). In this example, two cameras are used, a right and a left camera. FIG. 2A illustrates the fields of view of these cameras at an image of row 10. In some embodiments, the fields of view of these cameras can overlap. FIG. 2B shows the exemplary situation that allows the images to be captured. As drawer 110 is closed, row 130 passes through the field of view of image capture system 140, allowing successive images to be taken. FIG. 2C shows an exemplary grayscale image that can be captured, showing an overhead image of row 7 and oblique images of rows 6 and 8. Similar images can be captured overhead rows 6 and 8 as the drawer is closed. FIGS. 2D-2F illustrate the subsequent oblique perspective image (e.g., as shown in FIG. 2F) of row 7 (and overhead image of row 8, and oblique perspective image of row 9) that is captured as row 7 is advanced further into the work envelope 105 and as row 8 is centered or substantially centered beneath the one or more cameras. The series of FIGS. 2A-2F illustrate the depth of information that is obtained from the images, enabling the determination of the following characteristics: a center point of each tube in set 130 (e.g., the x-y location determined by correlating image features corresponding to a tube holder); a height of each tube 130 (e.g., correlated to the pixel distance of the top of the tube between two adjacent images); a diameter of each tube (e.g., by observing the pixel size of the circle or oval formed at the top of each tube or by the pixel distance between each side of the tube in each image); if a tube 130 has a cap or tube-top cup on its top surface; identification information on a tube 130 (i.e., an identifier, such as a barcode, placed on a cap of a tube 130); or other characteristics that will be apparent to a person of ordinary skill.

In some embodiments, one or two dimensional barcodes/QR codes can be placed on tube caps or on the surface of a tray. The images captured via image capture system 140 can be processed to read this information. This can reveal the identity of sample contained in a sample tube or information about the properties of the sample, such as the type of bodily fluid contained or whether the sample is high priority. In some embodiments, the color of the cap can indicate priority, type, or other status information, and can be determined by processing images captured by the image capture system. In some embodiments, the color or label observed by the image capture system can indicate that the sample tube contains a calibrating fluid or control.

In some embodiments, multiple types of trays can be used. For example, larger trays can be used to transport a greater number of sample tubes, while smaller trays may be used to transport a smaller number of samples, which may be useful when transporting specialized sample tubes, such as calibrators and STAT samples. The type of tray can be conveyed to the image capture system 140 via optical marks like QR codes on the tray. QR codes or other optical marks can also convey tray orientation, tray priority, identity/serial number, size, physical properties (such as number of slots, version, etc.) to the image capture system. By analyzing images captured of the marks, the drawer vision system can quickly anticipate the extent of a tray and better analyze the images of tubes, in some embodiments, by using a model of the tray based on information received from the optical marks.

In some embodiments, when the sample tube lacks a cap, the images captured via image capture system 140 can be processed to determine information about the quality of the sample and any defects or anomalous characteristics of a sample tube or tray at an early stage in the process. For example, peeling labels on the side of a sample tube can cause problems with subsequent handling. A peeling label may be visible in the top-down or oblique images if it does not lay flat on the tube surface. If a tube is wet or has condensation, it may cause problems with gripping. Condensation droplets may be observable as refractive or reflective beads if severe enough. If a tube has crack or other physical defect, this can be observable and detected during image analysis of the top-down or oblique images. Image analysis can also detect that a tube is tilted relative to other tubes, which may be useful in positioning the sample handling robot arm when it interacts with the tube.

If a sample has been mishandled, it can froth or bubble. This may affect readings later and can be detected via image analysis. Frothing or bubbles may be detectable in the top-down or oblique images if the condition is severe enough, and the system can alert the operator that a new sample may be needed. In some embodiments, anomalous qualities of a sample can also be detected. For example, a heterogeneous image or object in a tube may indicate debris or sample contamination, if severe enough to appear in an image. Other qualities can also be observed. An estimation of fluid height can also be determined by image analysis of the top-down or oblique images, which may provide an early alert that additional fluid volume may be needed. In some embodiments, errors about the condition of trays can be determined via image analysis of the top-down or oblique images. For example, the presence of a spill in a slot on a tray may be determined if a sheen or other optical anomaly is observed. Similarly, the presence of debris or an object can be determined if the normally pattern consistent with a tube or empty slot is not observed, but anomalous content is. Furthermore, if marks or structures in a tray are outside of expected patterns (such as barcodes or QR codes or localization markers), this can indicate that the tray is worn or damaged. An operator can be alerted if any these conditions exist.

These characteristics are obtained with no contact with the tubes 130, the tube tray 120, or the drawer 110. Instead, by obtaining images in different perspectives, stereoscopic analysis can be performed on the images. For example, the height of a tube 130 may be determined by comparing how much the center of a tube top shifts between subsequent images. In a similar manner, various other characteristics of the tubes 130 and the tube tray 120 may be determined.

Figure 3:
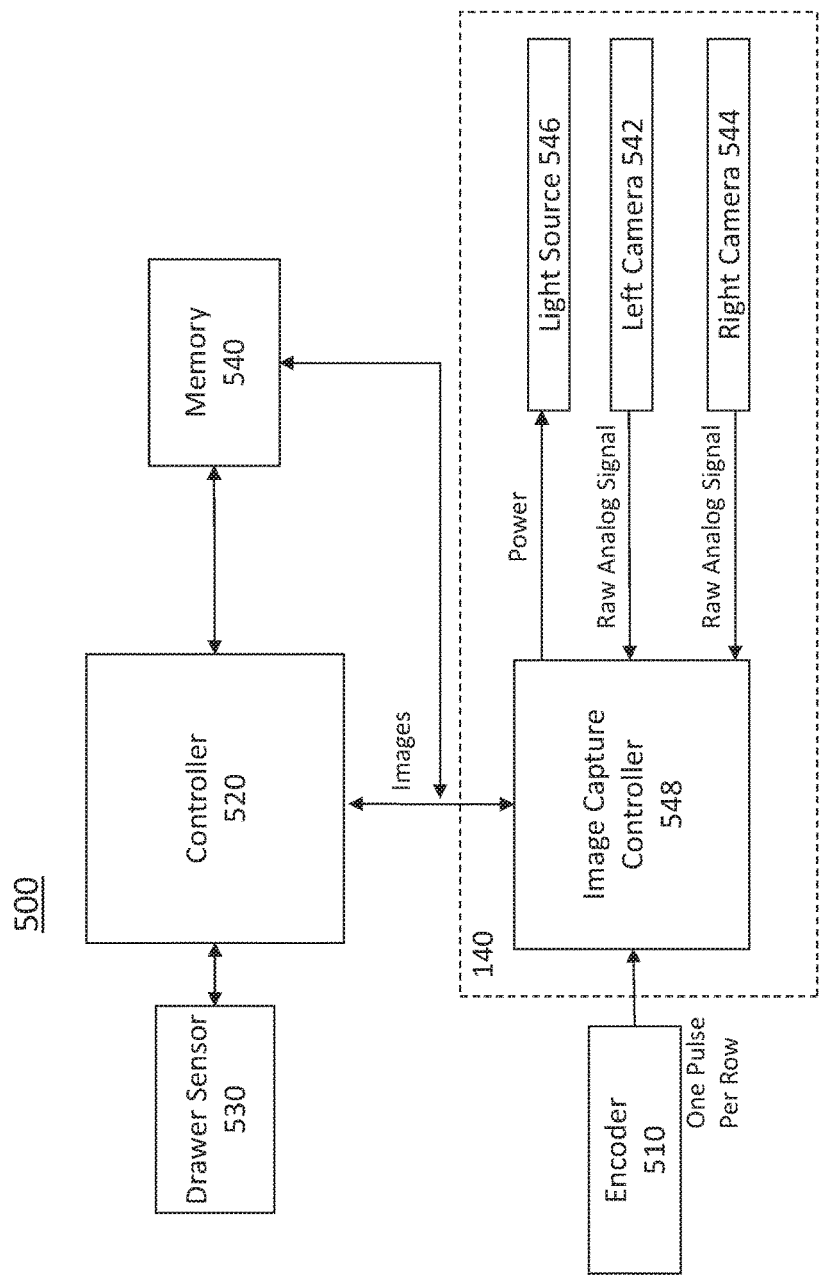
FIG. 3 illustrates a block diagram representation of a system for characterizing tube trays and tubes held in a drawer through image analysis, according to an embodiment.

Systems that utilize overhead cameras for characterizing tubes in a tube tray in any of the manners described herein can be referred to as a drawer vision system (DVS). FIG. 3 shows a block diagram representation of an exemplary DVS system 500 for characterizing, through image analysis, the tube trays 120 and the tubes 130 contained thereon held in a drawer 110, according to an embodiment. The image capture system 140, according to an embodiment, includes two cameras, a left camera 542 and a right camera 544. Additional or fewer cameras may be included depending on the size of the drawers 110 and the tube trays 120, as well as the desired image quality and image perspective. A light source 546 and an image capture controller 548 are also part of the image capture system 140.

In an embodiment, in order to accurately capture the image and taking into account that the drawer 110/tube tray 120 is moving, the cameras 542, 544 use a shutter speed fast enough to essentially produce stop motion photography for capturing the images. In some embodiments, the light source 546 may be synchronized with the triggering of the cameras 542, 544 to aid in strobe or stop motion photography. In other embodiments, the light source 546 may be on continuously or may be triggered on upon a first detection of movement of a drawer 110/tube tray 120. In some embodiments, cameras that are capable of a 250 microsecond exposure time are used. In other embodiments, cameras with other capabilities may be used depending on, for example, lighting, the speed of the drawer 110/tube tray 120, and the desired quality of the images.

With further reference to FIG. 3, an encoder 510, such as a quadrature encoder, is used to determine when a row of the tube tray 120 is moved into a centered or substantially centered position beneath the one or more cameras 542, 544. The encoder 510 transmits a signal (i.e., a pulse) to the image capture controller 548 upon detection of movement of the tube tray 120 corresponding to a new row of the tube tray 120 moving into a centered or substantially centered position beneath the one or more cameras 542, 544. The detection is based upon the encoder 510 incrementing upon a notch that indicates that the drawer 110 and/or the tube tray 120 has been moved one row. The signal serves as an instruction for the image capture controller 548 to instruct the cameras 542, 544 to take an image upon receipt of the signal. As described above, in some embodiments, the encoding scheme may correspond to other movements, such as, for example, the drawer 110/tube tray 120 moving two rows or the drawer 110/tube tray 120 moving into a position centered between two rows. The image capture controller 548 manages the storage of the images taken by the cameras 542, 544 during a time period in which the drawer 110/tube tray 120 is being moved into the work envelope 105. This time period may also include the drawer 110/tube tray 120 being moved out of the work envelope 105 (e.g., the drawer 110/tube tray 120 may be pushed into the work envelope 105, partially pulled out of the work envelope 105, then pushed back into the work envelope 105). One or more internal or external memory devices may be associated with the image capture controller 548, such as memory 540. In one embodiment, one of the one or more memory devices comprises random access memory (RAM) in which a table is stored, the table containing the images taken by the cameras 542, 544. The image capture system 140 may capture additional rows of images at the beginning and end of each drawer 110/tube tray 120 in order to ensure that all rows in the tray are seen from the same number of perspectives (otherwise the rows at the end will not be captured from one side). Additionally, the image capture system 140 may capture extra rows of images for all rows in order to generate additional perspectives on each tube and to aid in the determination of certain features. The image capture system 140 may also capture extra rows of images in order to detect features in the sample handler work envelope 105 in order to localize the trays 120 within the work envelope 105 and auto-calibrate the trays 120 to the sample handler's coordinate system. The image capture system 140 captures a fixed number of rows of images, at predetermined locations that have a fixed relationship to features of the trays 120 and sample handler work envelope 105.

The image capture system 140 may capture and store a single image corresponding to each imaging of a predetermined imaging position for the tray. For example, if a tray has 10 rows, and each row should appear in three adjacent images to provide two oblique perspectives and one substantially central perspective of each row, twelve images of the tray taken at twelve sequential imaging positions can be stored. When a new image of a particular perspective for a given row is captured, the previously stored image corresponding to that imagining position is overwritten. For example, consider the following scenario: an image is captured when row 10 is pushed into the drawer 110 and is centered or substantially centered beneath the cameras 542, 544 of the image capture system 140. If, subsequently, the drawer 110 is pulled out and then pushed in so that row 10 is again centered or substantially centered beneath the image capture system 140, a second image of this perspective is taken. This second image overwrites the first image. This implementation results in a fixed amount of storage as well as a fixed amount of processing time.

In some embodiments, images can be buffered until a drawer is fully closed. The buffering of images until the drawer 110 is fully closed and triggering the cameras 542, 544 on fixed positions can overcome challenges associated with random drawer movement. In particular, images are not acquired unless a fixed position of the drawer 110 is centered or substantially centered beneath the one or more cameras 542, 544, causing slight movements, such as an accidental bump, of the drawer 110 to be ignored by the image capture system. As a result, a set of images taken at predetermined imaging positions relative to the drawer is available for subsequent processing to determine characteristics of tubes and the drawer.

A controller 520 is provided for managing the image analysis of the images taken by the cameras 542, 544. Upon detection of the closing of the drawer 110, the image capture controller 548 provides the images to the controller 520 for downloading and processing. The controller 520 is, according to an embodiment, part of a sample handler that is used in the IVD environment to handle and move the tube trays 120 and the tubes 130 between storage locations, such as the work envelope 105, to analyzers. The image analysis performed by the controller 520 serves to instruct the sample handler on the various determined characteristics of the tube tray 120 and the tubes 130, thus allowing the sample handler to accordingly handle and process the tube tray 120 and the tubes 130.

The one or more memory devices 540 are associated with the controller 520. The one or more memory devices 540 may be internal or external to the controller 520. One or more drawer sensors 530 may be connected to the controller 520 to indicate when the drawer 110 is fully closed and/or when the drawer 110 is fully opened. According to an embodiment, the drawer 110 being fully closed serves as an indication to begin image processing of the captured and stored images. When the drawer 110 is fully closed, the drawer sensor 530 sends a signal to the controller 520.

Figure 4:
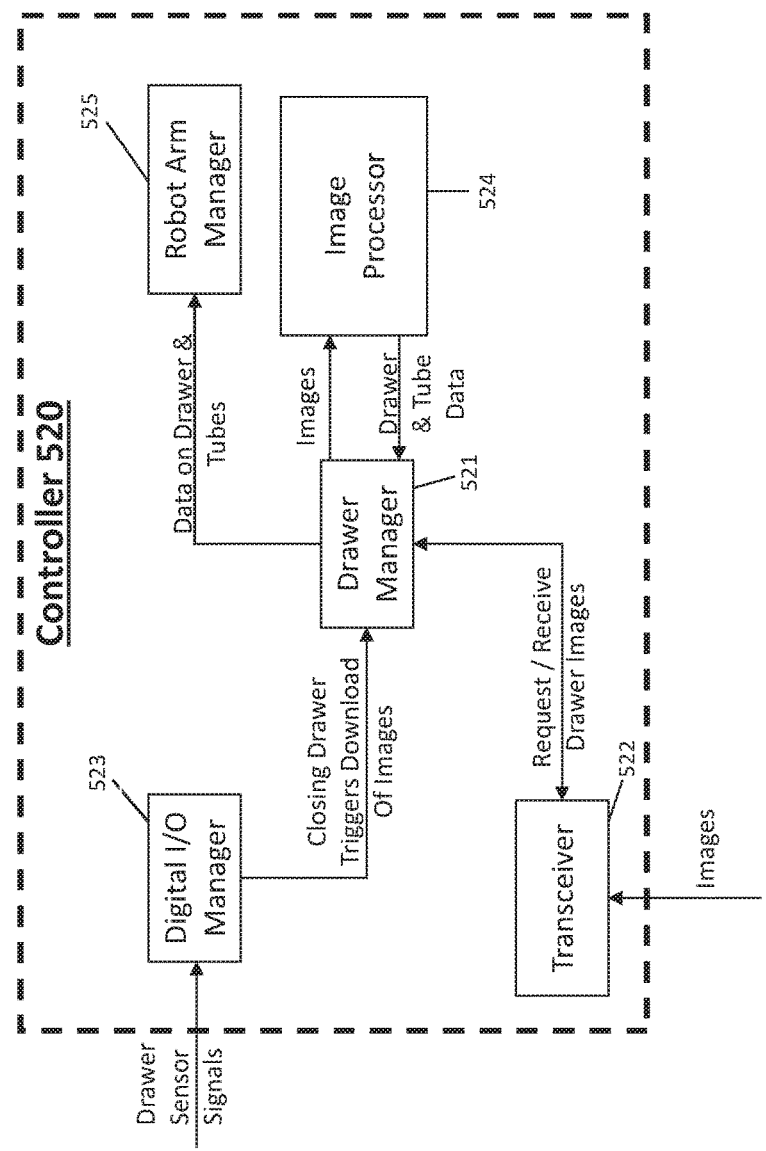
FIG. 4 shows a block diagram representation of a controller of the system shown in FIG. 3.

FIG. 4 provides a block diagram representation of the controller 520, according to an embodiment. A drawer manager 521 manages the data flow amongst the various modules of the controller 520. A transceiver 522, which may, according to some embodiments, be a USB transceiver, receives data (i.e., the images captured) from the image capture controller 548. A digital input/output (I/O) manager 523 manages the receipt and transmission of signals between the drawer sensor 530 and the controller 520. When the I/O manager 523 receives a signal from the drawer sensor 530 indicating that the drawer 110 is fully closed, the I/O manager 523 conveys this signal to the drawer manager 521, which issues a request to the transceiver 522 to download the images. The drawer manager 521 provides the downloaded images to the image processor 524 for processing thereof. The data processed by the image processor 524, which includes the characteristics of the tube tray 120 and the tubes 130 thereon, may be sent to a robot arm manger 525 via the drawer manager 521. The robot arm manager 525 is the module of the controller 520 that is associated with handling and transport of the tube tray 120 and the tubes 130 (i.e., the sample handler). Thus, the robot arm manager 525 utilizes the data processed by the image processor 524.

The image processor 524 processes, according to an embodiment, the images based on a first-in/first-out algorithm. Thus, the robot arm manager 525 may be processing/handling the tubes 130 of the first row while the image processor 524 is processing the images related to the second row. Since the robot arm manager 525 does not require all of the characteristics data at the same time, the image processor 524 is not required to have all of the image data processed by the time the robot arm manager 525 is ready to begin its functions. According to an embodiment, the time required for the robot arm manager 525 to process a row of tubes 130 is approximately 3 seconds, thus allowing the image analysis performed by the image processor 524 to take up to 3 seconds per row. Thus, while the image capture is real-time, the image analysis is not real-time. This greatly reduces the required processing speed and capabilities of the image processor 524.

To provide the functionality of a DVS, software that operates operating on one or more processors (such as image processor 524) that process the images needs to be tailored to handle the types of images seen in a drawer system. It is desirable that the software be calibrated to account for physical/optical camera properties and be further trained to recognize tube situations from real-world images.

In some embodiments, there are two parts of a DVS from a software standpoint: an online part and an offline part. Online refers to those parts that happen during operation, i.e., when the system processes the new images captured by the camera, and when the system is being used for discovering the drawer inventory during operation in the lab. Offline refers to any training and calibration of the DVS, done prior to operation on samples in a normal laboratory workflow. Generally offline steps are carried out at manufacture and possibly occasionally during the life of a DVS to maintain calibration. Online steps are carried out on a frequent basis as the DVS operates in a laboratory processing samples.

Offline training is particularly helpful for determining different tube types. Once a scope is defined to determine the tube types which are to be used for the system, images of those tubes can define a collection for the training. For training, it is desirable to have a large amount of data for training classifier components that allow the DVS to detect different tube types. The training can be done once at the factory, and may or may not be repeated at the customer's premises. Training on premises would allow a customer to customize the image training to the tube types and sizes used in a particular lab. In a rough sense, training can be thought of as something that happens on the manufacturer side. In some embodiments, training can occur once for the software package that is shipped with all instances of a DVS, while in others, the training can be tailored to each instance of the DVS. The other offline component, calibration, can happen at the customer's site or at the manufacturer of each instance of a DVS. Whereas training relates to interpreting the salient features in images that are captured by the cameras of a DVS, calibration relates to characterizing the physical and optical properties of those cameras to assist in interpreting images. Because each DVS is a separate physical device, each could have enough physical variance to warrant calibration of each DVS device. Therefore, in some embodiments, calibration is done on each DVS when it is installed at a customer site or after manufacture of a DVS, while training data can be preloaded. Retraining can also be later performed in some embodiments.

Figure 5:
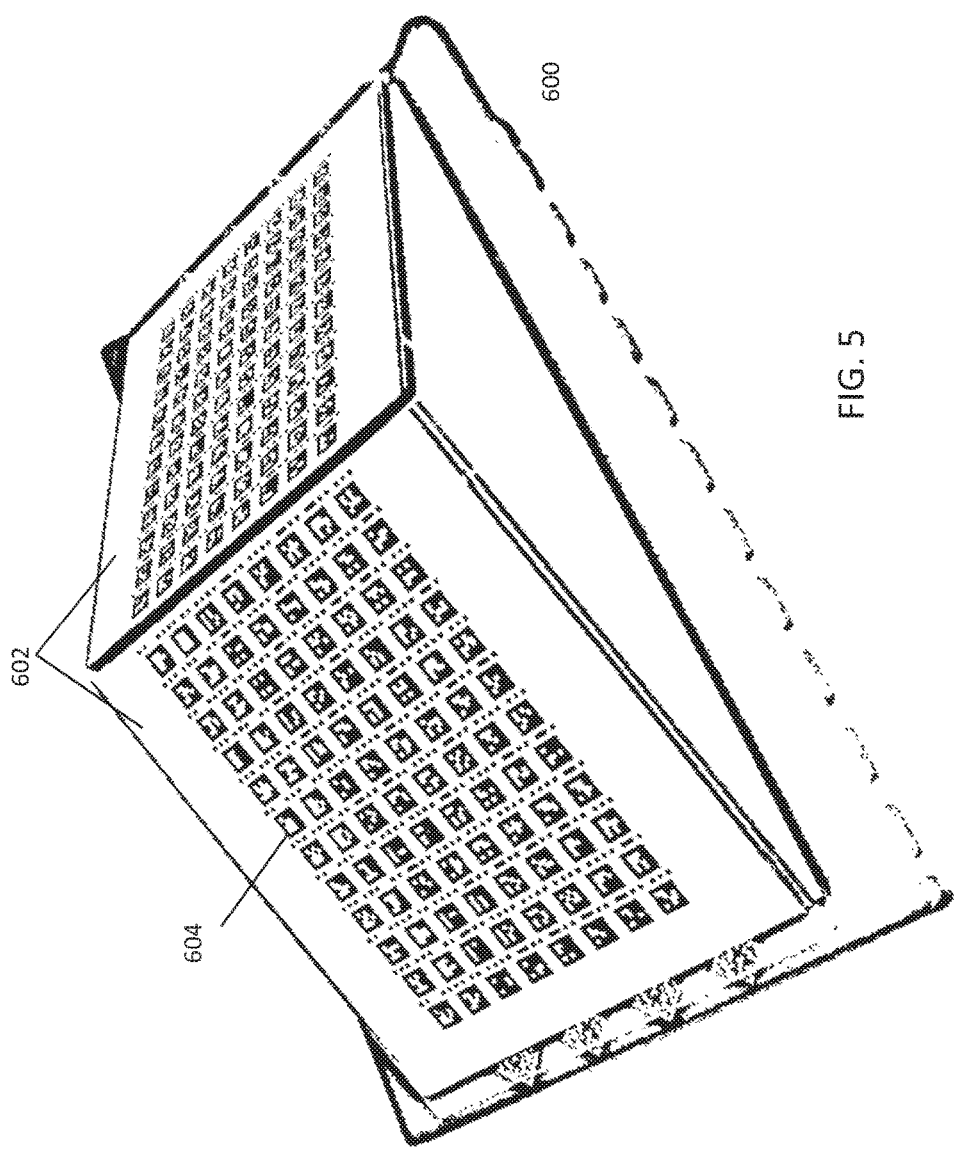
FIG. 5 is a perspective view of a calibration target for use with some embodiments.

Calibration can be done using a series of markers. FIG. 5 shows exemplary markers that can be used for calibrating cameras in a DVS. Calibration target 600 includes a plurality of planes 602. Each of planes 602 includes an array of unique markers forming a larger optical pattern. Exemplary individual markers 604 include Siemens Hoffmann markers. Planes 602 allow calibration target 600 to present a 3-D arrangement of unique markers 604. Siemens Hoffmann markers are useful for calibrating cameras by providing known 2-D space points relative to the image plane. Each marker 604 is a unique coded block that correlates to a unique location on each plane 602. By providing multiple planes of these markers, target 600 presents a plurality of known 3-D space points that can then be correlated to 2-D points in the image plane of each camera. Because each marker is unique, a camera can identify a grid location on each plane when only a partial view of the plane is available. Conventionally, chessboard patterns or Siemens Hoffmann markers are used in a single 2-D plane, often placed in front of the camera at various poses and distances. Multiple planes ensure that the markers on the planes present a three-dimensional target for camera calibration, where the pose of each plane varies relative to each camera as the calibration target slides past cameras in a DVS. In some embodiments, planes may be arranged in a pyramid or other shape to present a 3-D target for camera calibration.

Planes 602 may be mounted on top of a conventional tube tray, allowing calibration target 600 to be handled by a DVS during training in the same manner in which a tube tray would be handled at runtime. This allows motion mechanisms to move markers 604 relative to the cameras in the DVS. This further allows each marker to be placed at different locations in the image plane of each camera, in much the same way that salient features of a sample tube would be positioned in the image plane of each camera during runtime operation of the DVS. By utilizing an array of markers on a 3-D planar surface, multiple 3-D locations can be easily tested for calibration by sliding target 600 through the drawer system and capturing multiple images. This allows calibration images to simulate different tube top heights, for example. In some embodiments, the DVS includes multiple cameras aligned in a row in the drawer. The direction of that row is parallel to the peak in this calibration object. This calibration object works with one camera, as well as multiple cameras, as long as the camera can see the calibration object.

Each camera has two different types of properties. The first is called the intrinsic properties or parameters, for example, the focal length. In addition to the focal length, the intrinsic parameters of the camera also have a defined principal point, i.e., the optical center with respect to the image. The second is called extrinsic properties, which includes properties that change depending on the use of the camera, such as the pose—where the camera is facing and oriented with respect to a predefined coordinate system. Intrinsic and extrinsic properties should be calibrated.

By utilizing a calibration target, such as target 600, multiple cameras can undergo intrinsic property calibration at the same time. In addition, because multiple cameras see the same unique targets, extrinsic properties relative to one another can also be calculated using these targets. For example, a first camera can be used as a reference, allowing a second camera's pose to be estimated with respect to the first camera. Meanwhile, the locations of targets can be used to determine intrinsic parameters, such as the principal point of each camera. Target 600 is therefore designed to estimate intrinsic parameters of each camera.

Calibration is typically done by placing a plane in front of the camera and varying the pose of the camera or plane. In the DVS, space is limited, due to the drawer-like structure. By mounting calibration target on a tube tray, or an object simulating a tube tray, targets described herein can be used to calibrate DVS cameras in limited space. Ideally, only one image of the grid with non-coplanar 3D points is required for the purpose of calibration. However, it is often the case where only a subset of grid markers is visible within the limited field of view of the DVS camera. In addition, multiple observations of the grid placed at different locations with respect to the camera also greatly help improve the accuracy of calibration. With the cameras fixed, the drawer and target move, allowing the camera to take multiple images, which further allows a 3-D target with known coordinates to move around in the image plane. This results in multiple poses of the target relative to the camera, allowing sufficient data to calibrate each camera. Because a calibration target is large enough to be visible across multiple cameras, calibration software can derive the relative pose between each pair of cameras, in addition to the intrinsic properties of each camera.

Software used for calibration obtains the intrinsic and extrinsic properties of a camera via a set of known 3D points $\{P^j\}$ and its 2D correspondences $\{p_i^j\}$ on the i-th image. This is achieved by minimizing the re-projection error between the 2D projections and corresponding measured points. That is $$K, \{R_i\}, \{t_i\} = \operatorname{argmin}_{K, \{R_i\}, \{t_i\}} \Sigma_i \Sigma_j \| p_i^j - f(R_i P^j + t_i, K_c, d_c) \|^2, \quad \text{(Equation 1)}$$

One can decompose the R and t components separately, deriving a rotation matrix R and a translation vector t. R can be presented as a 3×3 matrix, while t can be presented as a 3×1 vector where f(.) is the 3D to 2D projection function that projects a point from the camera's coordinate system to its image plane, $K_c$ is the 3×3 intrinsic calibration matrix containing the focal length and skew of camera's two axes and the principal point on the image, and $d_c$ is its lens distortion vector. $R_i$ and $t_i$ are the extrinsic parameters describing the pose of the camera in the i-th image, where R is rotation and t is translation, represented with a 3×3 matrix and a 3×1 vector, respectively. There are six degrees of freedom to orient to the camera and appraise the camera. Equation 1 requires knowledge of the 3-D location of each marker. Because each marker is on a well-defined plane on a preconfigured calibration target, the 3-D location of each marker can be easily derived from knowledge of the construction of the target. Optimization can be carried out by using conventional software tools, such as, OpenCV API, to derive the intrinsic parameter for the camera and the extrinsic parameters for each image acquired by the camera.

To perform calibration, one simply runs the calibration target through the drawer and captures images. Because the location of each marker is known in 3-D space relative to the tray, and the position of the tray in the drawer as it closes can be derived easily through indexing or other means, this provides sufficient information for the algorithm in equation 1 to interpret the images and resolve the K, and t matrices. Because each marker is unique, the point in 3-D space corresponding to a marker can be determined for each two-dimensional image captured by a camera, even when the field of view does not capture the edges of the planes of the calibration target. The known 3D points $PjP_j$ are located relative to the tray; point $pjp_j$ is the point in the 2D image. Thus, the markers in the images provide known points P and p.

Given the poses $R_A$, $t_A$ and $R_B$, $t_B$ of Camera A and B estimated from a pair of images taken at the same time, the relative pose between the Camera A and B can be derived by:

$$R_{A \to B} = R_B R_A^{-1} \quad \text{(Equation 2)}$$

$$t_{A \to B} = t_B - R_B R_A^{-1} t_A. \quad \text{(Equation 3)}$$

Once we have two cameras, the calibration parameters are estimated for each camera. Equations 2 and 3 just tell you how to derive the relative pose between camera A and B. This is the conventional approach to deriving the relative pose. $R_A$ is characterized here as $R_A^{-1}$ because you need to reverse the rotation back to a coordinate and then re-project back to another coordinate system. It is an inverse of the matrix.

Note that the aforementioned calibration is performed based on a target with known 3-D points, which can be provided by the 3-D coordinates of each calibration point on the target. As calibration points on each marker plate lay on a regular grid of a planar surface, their global coordinates can be described as a rigid transform of their local coordinates. Images taken from a single camera with various placement of the whole calibration target in the field of view allows calibration of these 3D coordinates. The rigid transform between these two plates of the target can then be derived via a non-linear least squares optimization to infer the 3D coordinates of all calibration points on the target.

Once a camera is calibrated, it can be used to train an image detection algorithm to utilize these parameters to interpret real-world images of sample tubes in tube trays, allowing optical characterization of the contents of each tube tray in the DVS system. In some embodiments, the training process uses actual bodily fluids in tubes, whereas in other embodiments, simulated bodily fluids are used for health and safety purposes. For example, blood can be simulated using a scarlet fluid of a similar viscosity to blood. Images can be captured of simulated or real fluids in exemplary sample tubes in a tube tray. These training samples can be prepared to simulate real world samples by varying the fill heights of tubes. The sample tubes used can be of the same type, such as height, diameter, material, etc. of sample tubes that will appear in a laboratory environment. A variety of fluid types can be used, including serum, blood, and urine, which each may be simulated. In some embodiments, a greater proportion of the training samples can be serum, which may better approximate real-world usage.

A test harness comprising an exemplary DVS system and a tube tray containing a variety of training sample tubes can be used to train the image processor. The tubes can include a variety of different tube positions, and may include markers on the tray that may encode a ground truth about the characteristics of each sample tube. This allows one or more training trays to be slid into the DVS, allowing the cameras to capture a plurality of images from various angles of each tube. These images of tubes can be divided into image patches corresponding to each tube, allowing a random forest classification algorithm to be run.

In some embodiments, the image patches corresponding to each tube are resized to 64×64 pixels, to provide normalized training image patches. This normalization may be necessary to scale images where, due to distance, a portion of an image corresponding to a sample tube is smaller than the portion of the image corresponding to sample tubes at the image center. Distortion is already removed during the camera calibration process, because any lens distortion factor is resolved. In general, image patches are captured with any lens distortion already factored out. In some embodiments, these normalized image patches can further be rotated 90, 180, and 270 degrees to generate new patches that can be used during training, to add data variation. Fiducial marks, such as white dots placed on the surface of a tube tray, can be used to identify the row and column location of each tube within a tray. Fiducial marks in an image patch can identify which slot in the tray corresponds to the image patch or simply align the slots within an image by providing a reference point. This information can be helpful because cameras do not have the same viewing angle of each slot within a tray. For example, slots in the column near the edge of a tray may not pass directly under a camera, while slots in a column near the center of the tray may pass directly under a camera. Accordingly, slots corresponding to certain columns or rows may include steeper viewing angles in the image patches.

Image patches can include two types of image patches. A first type of image patch corresponds to the portion of an image that is centered at the tube top of each training tube. These image patches can be selected by running a conventional circle detection image processing algorithm on the image to identify probable tube tops. In some embodiments, where the algorithm is training for detection of the presence of a cap or tube top cup, image patches corresponding to a tube top can be scaled so that all tube tops are substantially the same size during classification training. The second type of image patch corresponds to the slot into which a tube can be inserted. By identifying the location of slots in the tray surface, such as by understanding the pose calibration of the cameras, as described herein or by using the assistance of fiduciary marks or other image features to identify the location of physical tray slots in an image, an image patch corresponding to the extent of that tray slot can be selected. If a tray slot is unoccupied, this image patch may show a clean circular structure corresponding to the slot; if a tray slot is occupied, this image patch may show an obstructed slot that includes a bottom portion of a sample tube.

Once images are collected and training image patches are generated using the test harness, a processor may proceed to feature extraction. For each image patch, the training algorithm computes a histogram of oriented gradients and steerable filter features. The algorithm can also compute the mean and variance of intensity values. After feature extraction, each image patch is represented by a high-dimensional feature vector.

In some embodiments, the trays include 2-D barcodes or data marks that are attached to the ends of a tray to identify the tray and/or the tray type. When a tray is initially inserted into a drawer a barcode near the end of the tray will appear in the initial images and can be identified through conventional pattern matching techniques to locate the barcode, or a barcode may be placed at a substantially uniform location on each tray. These barcodes may contain information about the tray type, which may identify the tray as having 15 or 55 slots. In some embodiments, a drawer is specifically designed to accommodate one 55-slot tray on a front portion and one 55-slot tray on a rear portion, or three 15 slot trays on each portion. Accordingly, if the identifying barcode is always located at an edge of a tray, only certain images are captured when the tray is inserted, corresponding to those boundaries between trays, need to be searched for and identifying barcode. Furthermore, orientation markers can be identified in these images to orient an understanding of the tray by the processor. Maintaining a proper model of the orientation and layout of a tray can be important for identifying the expected location of tube slots in an image.

By performing camera calibration using a calibration target, a processor has access to parameters for describing the radial distortion of the lens of the camera. This radial distortion can be compensated using these parameters, such that straight lines in 3-D will appear as straight lines in the undistorted compensated images. This compensation for distortion can facilitate tube slot alignment for patch extraction of both tray-level patches (e.g. tube slot patches) and tube-level patches (e.g. tube top patches).

Once the tray orientation type has been identified, the image processor can overlay a virtual tray slot grid into a model of the images. This grid can include an additional row and column to allow for identification of any fiducial marks on the tray surface. For example, a 55-slot tray would have a virtual 12×6 grid. This grid can be aligned with the tray surface by identifying any fiducial marks on the tray surface, where fiducial marks are arranged in a grid on the surface, such as between each set of four tube slots, and at the edges. This grid can then be used to assist in identifying image patches that correspond to tube slots. The grid allows images of a tray to be properly aligned for processing. To uniquely identify fiducial markers, a row index encoder that registers as the tray slides into the drawer can identify the physical translation of the tray. Each detected fiducial marker is associated with the nearest encoder marker and an average offset is calculated. This allows the tray slot grid to be reliably aligned with the tray images, even when only a few fiducial markings are available in an image without occlusions due to sample tubes resident in the slots.

After the tray grid is overlaid, the algorithm crops the tray slot patches. The camera images are captured with an encoder triggering the camera. If there is a tray in the camera's field of view, the captured image centers at a particular row. Given this information and the tray slot's row and column index, the algorithm computes the possible region of interest in the image and applies a circle detection algorithm to detect the tube top if there is a tube in the slot. If a circle is found, it crops the tube top level patch. The tube top patches along with the tray slot patches are used as input for the empty slot detector and tube type detectors. The patches along with ground truth are also collected to train the detectors offline.

An exemplary image and exemplary image patches extracted using this technique are shown in FIG. 6. Image 610 is an exemplary image that may be captured in the field of view of a camera in a DVS. Image 610 has been compensated for image distortion once the camera has been calibrated. White dots can be detected in the image and used to orient a grid overlay of the tray surface. Using this grid, image patches corresponding to tube tops 612 and tube slots 614. In this example, all tubes have caps, which can be identified using circle detection to derive image patches 612. Similarly, all slots are occupied, such that image patches corresponding to the locations of tube slots are obscured by portions of sample tubes. However, by orienting a grid relative to the tray surface the image processing, image patches 614, corresponding to occupied tube slots, can be derived for processing an identification of slot occupancy.

Image patches 612 and 614 can be used for training purposes, along with an identification of the ground truth of the tube top and slot occupancy. Similarly, during runtime in a laboratory, image patches 612 and 614 can be created by the DVS for processing an identification of tube top type and slot occupancy.

Figure 7:
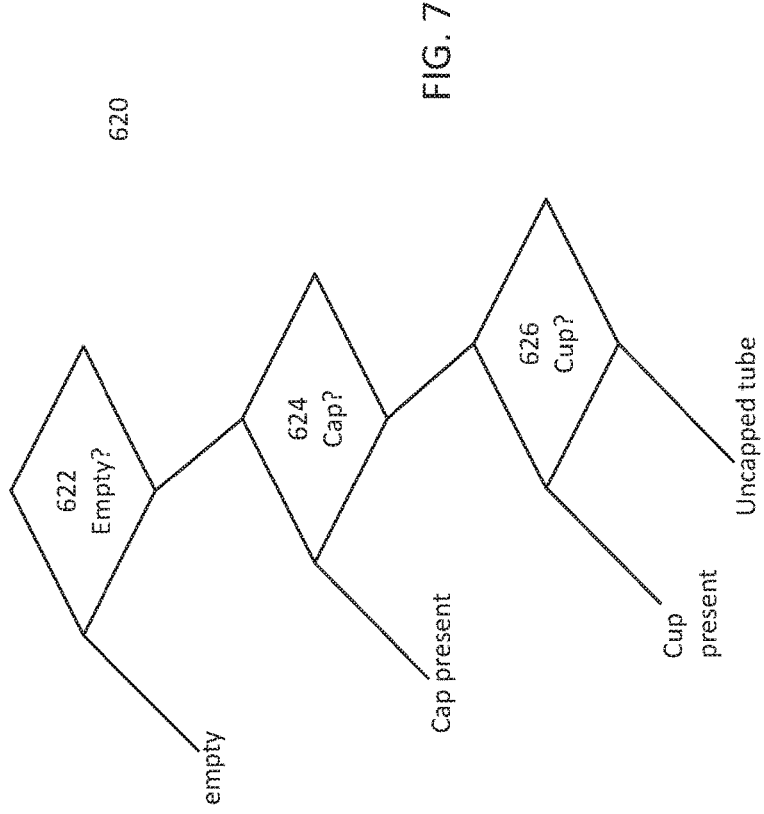
FIG. 7 is a flow chart of a tube classification scheme for use with some embodiments.

After tray slot in tube top patches are extracted they can be processed via detection pipeline in software to classify each tray slot as empty or non-empty, classify each non-empty slot as having a cap or not, and further classify each uncapped tube as having a tube top cup or not. The basic decision tree is shown in FIG. 7. The method 620 shows the basic process for characterizing the contents of a tube slot from image patches. At step 622, the image processor views a tray-level image patch corresponding to a tube slot and determines whether the patch indicates that the slot is empty or occupied. If occupied, at step 624, the processor views a tube level patch of the top of the tube occupying the slot to determine if a cap is present. If no cap is present, at step 626 the image processor determines from the tube-level patch if a tube top cup is present. In this manner, an image processor using the tray level and tube level patches corresponding to a slot to classify each tray slot to "empty" and "non-empty" categories, and classify each "non-empty" tray slots to "tubes with caps", "tubes with tube-top sample cups" and "plain tubes" classes.

The empty tray slot detection at step 622 comprises two steps. In the first step, the extracted tray slot patches from each input image are fed to a random forests classifier that is trained using empty slot patches and non-empty slot patches. Given the output score, each patch is classified to the "empty" class (if the score is less than $\gamma^{Empty}$) or the "non-empty" class (if the score is greater than $\gamma^{Empty}$). In the second step, the detection results on the patches of the same tray slot are fused over the time. This is because the tray slot is seen in the camera multiple times while the drawer is moving. In one embodiment, each slot is seen at least three times within a drawer closing action. An algorithm calculates a weighted average of the prediction score from each patch. The slot is classified as "empty" if the average score is less than $\gamma_{Slot}^{Empty}$ and otherwise as "non-empty," allowing the processing to proceed to step 624.

In some embodiments, there are three rows of tubes in the image plane that are analyzed in each image. A center row, closest to the image center of the camera includes tubes that are directly underneath the camera as the drawer is closing. A top row includes tube slots of that have already slid past the camera in the drawer, while the bottom row includes tube slots that have yet to pass underneath the camera in the DVS a drawer is closed, or vice versa. Thus, each tube slot can be analyzed three times as it passes the camera, providing three separate camera angles in three successive images of the tube slot. As part of the training process, and optimized a weighted average is created, allowing a weight to be assigned to each of the three tube slot positions. For example, an image patch associated with a tube slot in the central row may be given a higher weight because the central location of the slot in the image and substantially perpendicular camera view allows the tube slot in the central row image patches to be less obscured than image patches in the top or bottom row, due to the oblique angle at which these image patches are taken. In some embodiments, different weights can be assigned to tube slots in different columns as detection is optimized. For example, tubes in the center row, but not in the column directly under a camera may appear differently to the camera due to the oblique angle in which at tube slot is observed, off-center in the image. By utilizing a weighted average, a higher confidence level can be obtained for the detection step. This weighted average approach can be applied to each of steps 622, 624, and 626, or any of the other processing steps discussed herein.

Step 624 can comprise two steps. In the first step, the extracted "non-empty" tube top patches (classified from the step 622) from each input image are fed to a random forests classifier trained using tubes with caps patches and other patches. Given the output score, each patch is classified to the "tube with a cap" class (if the score is less than $\gamma^{Cap}$) or the "others" class (if the score is greater than $\gamma^{Cap}$). In the second step, the detection results of the same tray slot are fused by averaging the prediction score from each patch. The slot is classified as "tube with a cap" if the average score is less than $\gamma_{Slot}^{Cap}$ and as "non-capped tube" otherwise.

Similar to the empty slot detection, the processor can utilize patch location-based tube prediction. In the approach, the processor classifies the tube patches into three classes such that the patches at the central row (we call the classifier trained on the dataset as $Cap_{CR}$), the patches at the lower row (we call the classifier trained on the dataset as $Cap_{LR}$), and the patches at the upper row (we call the classifier trained on the dataset as $Cap_{UR}$). Because occlusion is not a problem at the tube top level, the processor collects three location patches and fuses the prediction using a weighted average. The location information is accessible because the DVS has an encoder device which triggers the camera to capture pictures at certain locations when the drawer is being closed. The locations are aligned with the drawer positions when each of the tray rows is at the image central row. The design allows that this is true without depending on the tray position and type.

The training of the three classifiers for each of the rows in cap detection uses a random forest technique. The prediction of the new patches of the tube in a non-empty slot is computed as follows at runtime:

$$p^{Cap}(t_{r,c}) = \alpha_{CR} * Cap_{CR}(t_{r,c}) + \alpha_{LR} * Cap_{LR}(t_{r,c}) + \alpha_{UR} * Cap_{UR}(t_{r,c}) \quad \text{(Equation 4)}$$

The subscripts r, c indicate the row and column indices of the tube. The weighting can use the average for a number and also can use the Gaussian kernel to weight the series classified based on the location. The weighting coefficients can be learned from the training data as well.

Step 626 is substantially similar to step 624, where the classifier has been trained to detect tube top cups, rather than tube caps.

An image processor can also estimate tube height from images captured by the cameras as tube slots pass. To estimate tube height, to successive images of the same tube, as the tube moves relative to the camera, can be used. The displacement within the image of the tube top between the successive images can be utilized to determine the tube height once the camera is calibrated. By assuming that the viewing direction of the camera is perpendicular to the tray surface, the tube height estimation can be carried out with a simple 2-D projection model. The displacement of 2-D projection is proportional to the physical displacement and inversely proportional to the distance from camera center. More formally, it is described by the following perspective projection model:

$$\Delta x = f \frac{\Delta X}{Z}, \quad \text{(Equation 5)}$$

In equation 5, f is the focal length, and Z is the distance between the 3-D point to camera's optical center, $\Delta x$ and $\Delta X$ are the 2-D and 3-D displacements of the 3-D point, respectively. When observing the 2-D displacements of two 3-D points traveling in the same distance in the direction perpendicular to camera's viewing direction, their relative distances to the optical center is independent of the focal length. Distance traveled can be determined based on the physical distance between successive images captured, which is affected by the encoding used in the DVS drawer system. The distance moved by fiducial marks within the image can be used for this purpose. That is, $$\frac{\Delta x_1}{\Delta x_2} = \frac{f \Delta X / Z_1}{f \Delta X / Z_2} = \frac{Z_2}{Z_1}. \quad \text{(Equation 6)}$$

Therefore, by tracking the displacements of dot markers on the tray surface, $\Delta x_{tray}$, and the center of a tube, $\Delta x_{tube}$, the tube height can be determined by:

$$\frac{\Delta x_{tube}}{\Delta x_{tray}} = \frac{\text{tray\_to\_camera\_dist}}{\text{tube\_to\_camera\_dist}} = \frac{\text{tray\_to\_camera\_dist}}{\text{tray\_to\_camera\_dist} - \text{tube\_height}}, \quad \text{(Equation 7)}$$

$$\text{tube\_height} = \text{tray\_to\_camera\_dist} \left(1 - \frac{\Delta x_{tray}}{\Delta x_{tube}}\right) \quad \text{(Equation 8)}$$

Image analysis by an image processor can also determine an estimation of the tube diameter for detected tubes. Based on the calibrated camera geometry, a diameter can be approximated for each detected tube, once a tube height has been estimated. This is made possible by the following relationship.

$$\text{diameter} = d * \text{depth} * 2 / (f_x + f_y) \quad \text{(Equation 9)}$$

In equation 9, d is the tube top diameter in pixels and depth=tray_to_camera_dist−tube_height. And tube_height is obtained from the previous step and tray_to_camera_dist is measured offline and obtained from the configuration file.

Furthermore, the image processor can estimate the tube center offset, which may be helpful for determining if a tube is tilting more for determining where in a tube slot the tube is located, if a tube slot does not have a centering spring to hold the tube. The tube center offset is estimated by computing the offset between the tube center in 3-D and the tray slot center in 3-D.

$$\Delta d = tube\_center - slot\_center \quad \text{(Equation 10)}$$

$$tube\_center = tube\_center\_image*(tray\_to\_camera\_dist - tube\_height) \quad \text{(Equation 11)}$$

$$slot\_center = slot\_center\_image*tray\_to\_camera\_dist \quad \text{(Equation 12)}$$

The image processor can also estimate the color of any caps by performing the color classification in SVG color space. For each of the pixels that correspond to where the cap is in the image, the processor maps the pixel into a color space and look for clusters. In some embodiments, the image processor estimates the color of the cap by fitting one cluster or two clusters of similar colors within the cap circle. The compactness of clusters is used to determine if there is one or two colors present. For example, some caps have multiple colors to indicate certain types of content.

Figure 8:
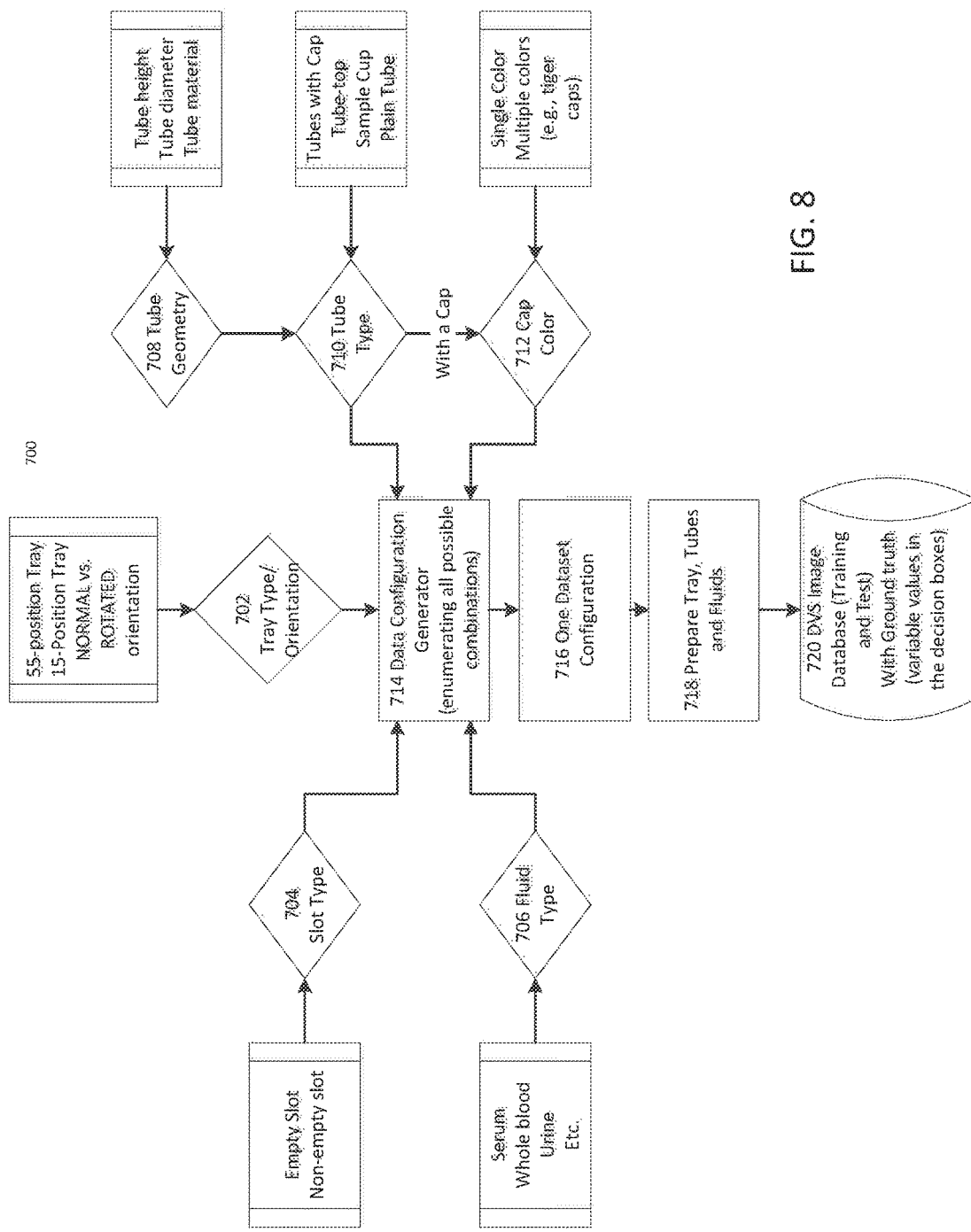
FIG. 8 is a dataflow illustrating the creation of a DVS database for use with some embodiments.

FIG. 8 depicts the data flow to create a DVS image database that can be used for training and testing of the image processing systems for the DVS. This database can be created prior to a training session. This can be done at the factory or at the customer site. A variety of data test cases should be used to fully train the DVS system. Tray type/orientation test cases 702 can include multiple types of trays, such as 55 position trays and 15 position trays, and various orientations that these trays might appear in a DVS drawer. Slot type test cases 704 includes slots that are empty and slots that contain a sample tube. Fluid type test cases 706 includes the variety of sample types that will be encountered in a lab, such as serum, whole blood, urine, etc. Tube geometry test cases 708 include a variety of tube heights, tube diameters, and tube materials that will be utilized in a laboratory environment. The test cases 708 may vary from custom installation to customer installation, or an enumerated list of available tube geometries can be utilized to train a superset of tube geometries at the factory. Tube type test cases 710 include tubes with caps, tube top cups, and playing tubes that are unadorned with caps or cups. For those tubes with caps, cap color test cases 712 can include single and multiple colors. In some embodiments, based on the desired test cases that may be selected in test cases 702 through 712, a processor automatically generates an enumeration of all possible combinations of these test cases to create a training sample plan using a data configuration generator 714. The output of data configuration generator 714 is a single data set configuration 716 that includes sufficient test instances to train the image processor to handle each of the test cases. At step 718, a technician will prepare trays having various tubes and fluids consistent with the data set configuration 716 determined by the processor. These sample trays are then run through a DVS test harness, or a DVS system as part of a customer instrument to prepare a plurality of test images consistent with data set 716. Database 720 includes ground truth for each test sample, allowing training.

Figure 9:
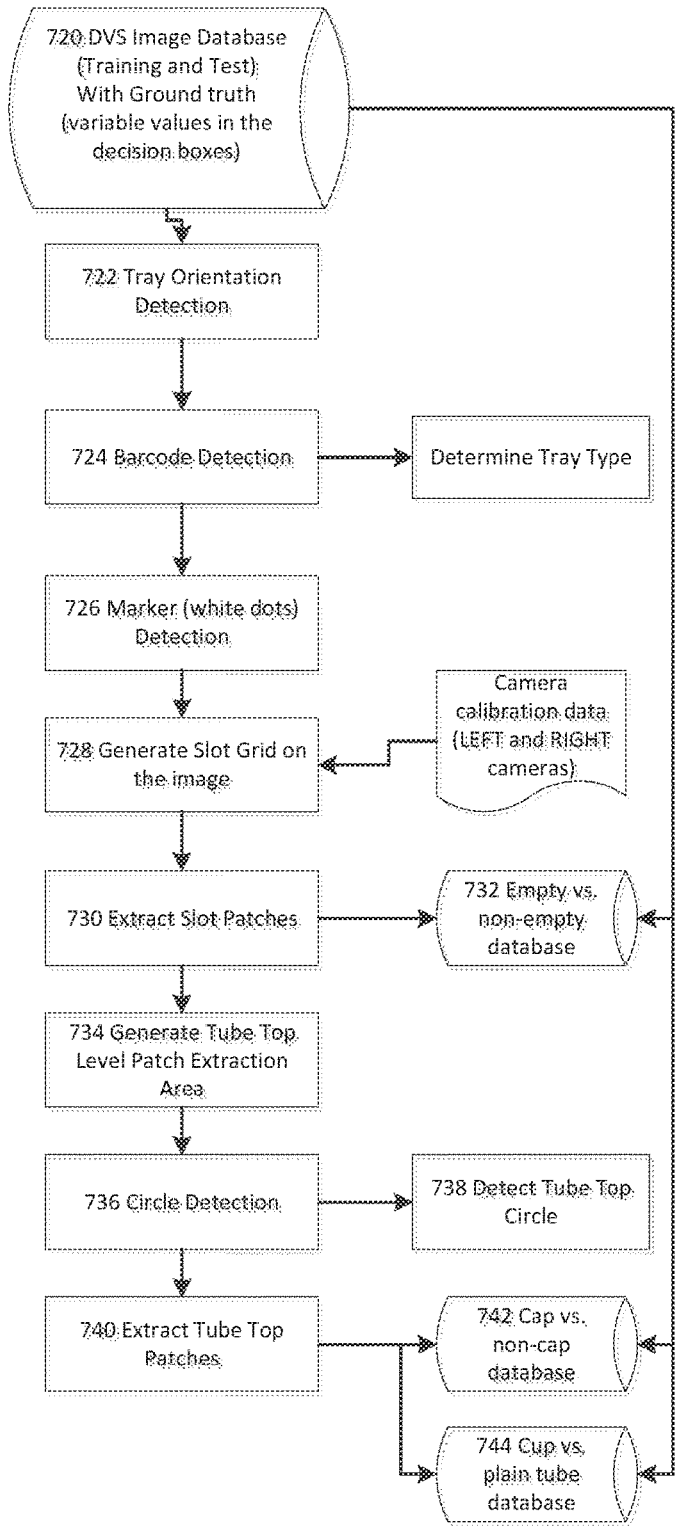
FIG. 9 is flowchart of the creation of a DVS image database for use with some embodiments.

FIG. 9 depicts the data creation process to create the DVS image database data using a DVS test harness or DVS. Once physical test trays that include the prescribed test case scenarios are loaded into the DVS, the DVS detects the tray orientation at step 722. This can be via optical means to detect the presence of corners or by physical means that detect the physical orientation of a tray inserted into a drawer. At step 724, barcodes at the edges of each sample tray are detected. This allows the DVS processor to determine the tray type, such as a 55 slot tray for which the images will correspond. At step 726, fiducial markers on the tray surface are detected. This allows the DVS processor to orient the physical location of salient components of the sample tray. At step 728, the processor generates a virtual slot grid that can be virtually overlaid onto images of the sample tray. This grid takes into account the camera calibration data of both DVS cameras. At step 730 the processor extracts slot patches, as described herein by identifying the location of slots relative to the fiducial marks. The image patches corresponding to those slots becomes training data that can be inserted into DVS image database 720. Specifically, the training data is empty vs. non-empty database 732, because the slot patches from the various images captured that are generated by step 730 include both empty and nonempty slots that can be used for training purposes. At step 734, the image processor generates a tube top level patch extraction area. This extraction area can be a search area that roughly correlates to the location of each slot and allows the tube top to be identified within this extraction area. At step 736, a circle detection algorithm is run within the extraction area to identify the precise location within the image of each tube top. At step 738, the tube top circle within the extraction area is identified. At step 740, the image processor extracts tube top patches that are centered about the tube top circles detected. These patches can also be normalized such that the extents of the patch correlates to the extents of the tube top circle. This process results in two databases, cap vs non-cap database 742 and cup versus plane tube database 744, because the tubes in the images should include cups, caps, and uncapped samples. Databases 742 and 744 become part of the DVS image database 720. In this manner a complete training set of image patches can be created using a DVS test harness or DVS system.

Figure 10:
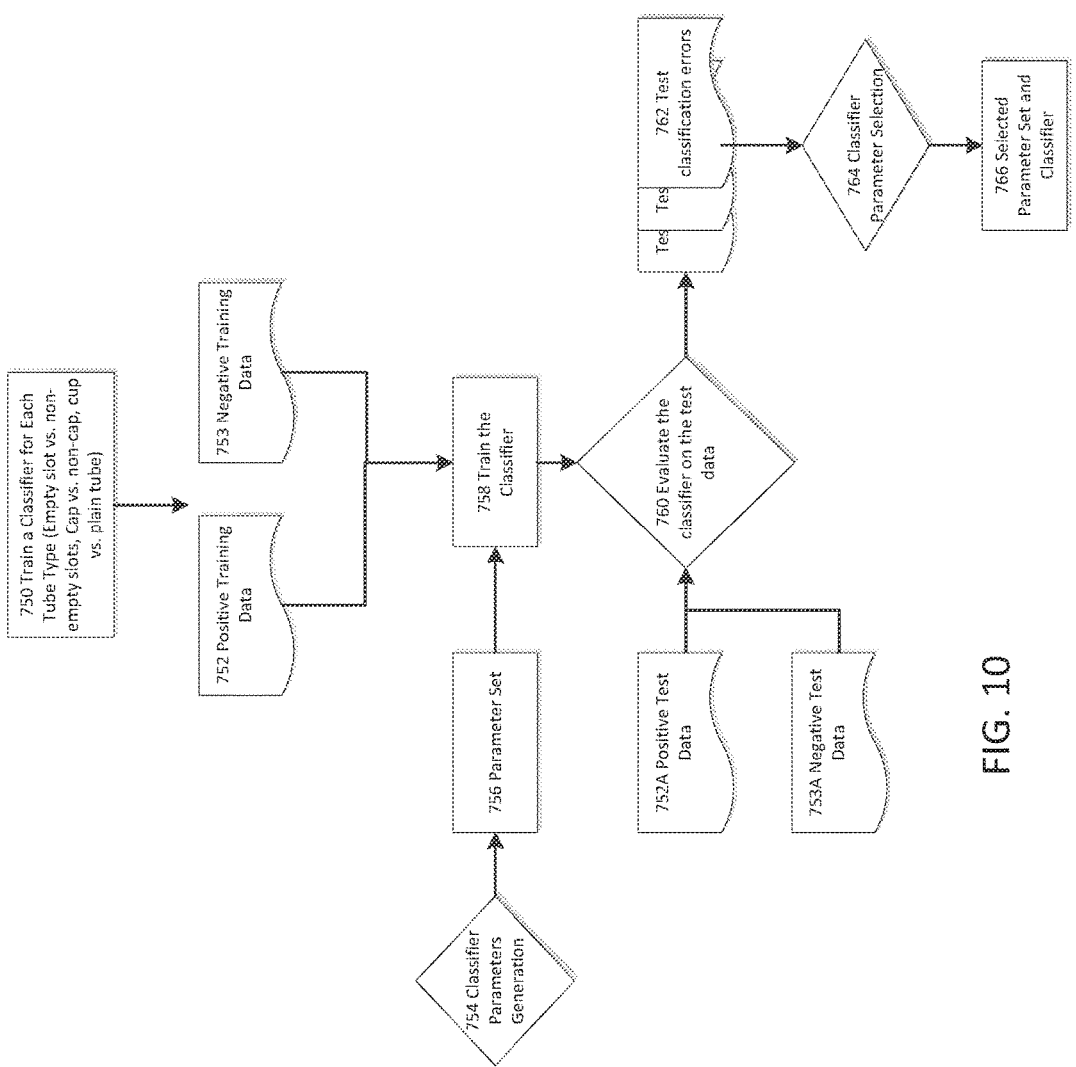
FIG. 10 is flowchart of classifier training for use with some embodiments.

FIG. 10 depicts the training process 750 for training the classifier for detecting any of the conditions in FIG. 7. Two sets of training data are created for each classifier. Positive training data 752 contains image patches where the condition being classified is positive, such as tubes having a cap; negative training data 753 contains image patches where the condition being classified is negative, such as tubes lacking a cap. Classifier parameters are generated by a process 754 operated by a processor. These parameters may be a best guess starting point for appropriate parameters for training of the classifier and result in a parameter set 756. The parameters in parameter set 756 can include parameters used to configure the random forest classification training algorithm, such as identifying a depth of tree of 10, a minimum sample count at the leaf note of five, the number of active variables at 100, and the maximum number of trees at 100. Parameters may also include $\gamma^{Empty}$, $\gamma^{Cap}$, $\gamma^{Cup}$, $\gamma_{Slot}^{Empty}$, $\gamma_{Slot}^{Cap}$, $\gamma_{Slot}^{Cup}$ and the weighting coefficients in the Equation 4. A processor performing the training trains the classifier using a random forests algorithm at step 758. This results in a trained classifier that can be evaluated using test data. Test data can be image patches similar to the training data. For example, sample image patches generated using the system of FIG. 9 can be divided into training data and test data to fully evaluate the classifier. Positive test data 752A includes image patches that contain the trait being detected by the classifier, while negative test data 753A includes image patches that do not contain the trait being detected by the classifier. At step 760, the training processor evaluates the classifier using the test data, which results in test classification errors 762. At step 764, the training processor optimizes the classifier parameters and selects appropriate parameters to minimize the classification errors. This results in a selected parameter set and a trained classifier data 766. This parameter set and classifier can then be used at runtime to detect each of the slot and tube conditions in FIG. 7.

Figure 11:
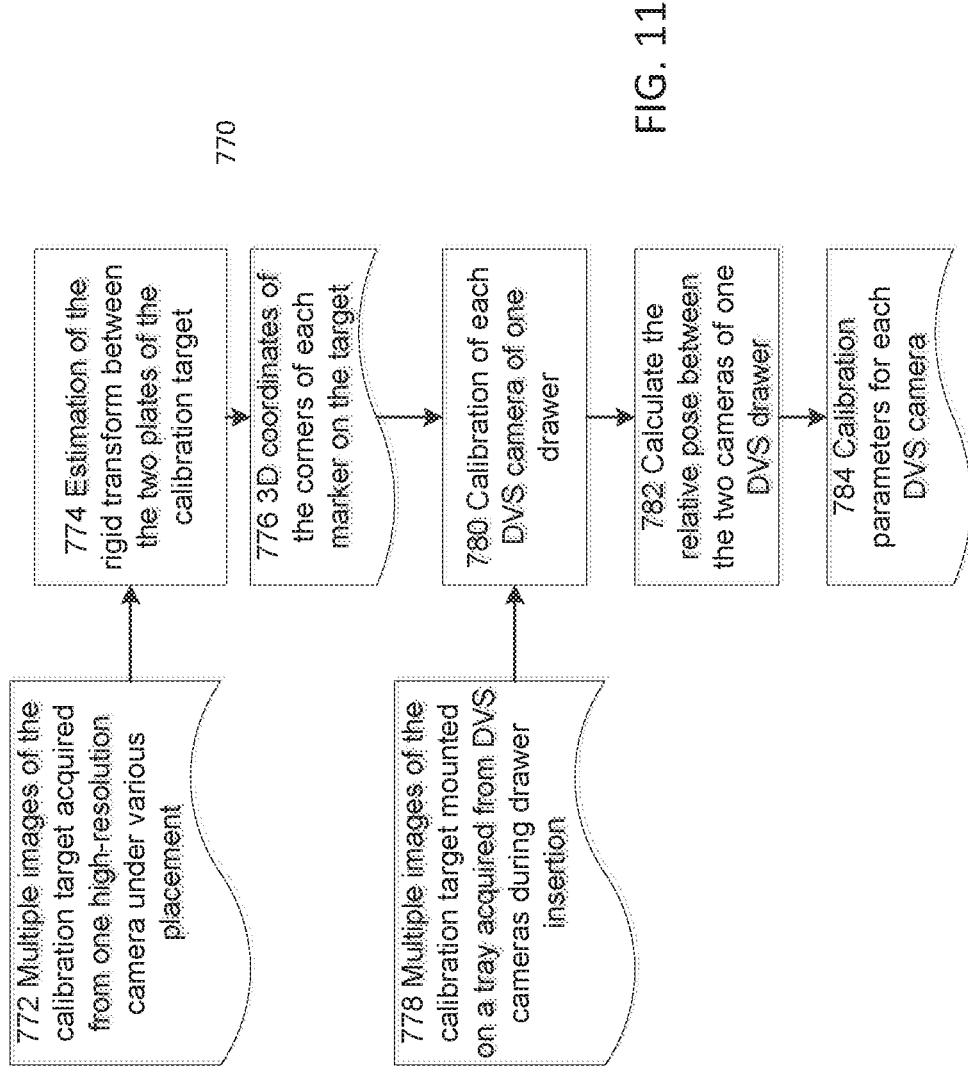
FIG. 11 is flowchart of an exemplary method of calibrating cameras using a calibration target for use with some embodiments.

FIG. 11 shows an exemplary method 700 for calibrating cameras utilizing a calibration target, such as that shown in FIG. 5. Using a previously calibrated high-resolution camera, multiple images 772 of the calibration target are acquired from each in the DVS. These images include multiple placements of the target to provide sufficient data to estimate the 3-D coordinates of the markers on the calibration target. At step 774, a calibration processor estimates a rigid transform between the plates of the calibration target and the pixel values in the image. This results in 3-D coordinates 776 that identify the corners of each marker on the target in 3-D space and provides a 3-D model of the calibration target that can be used in Equation 1. Once a 3-D model of the markers is available, cameras in the DVS being calibrated can capture multiple images 778 of the calibration target mounted on a tray and inserted in the DVS drawer. At step 780 the calibration processor utilizes 3-D coordinates 776 and images 778 of the DVS to be calibrated to calibrate each DVS camera of the drawer. This step can utilize the teachings discussed herein, such as Equation 1. At step 782, the calibration processor calculates the relative pose between the two cameras in the DVS drawer using the methods discussed herein, such as Equations 2 and 3. This results in calibration parameters 784 for each camera in the DVS system. This allows the DVS system to be trained and camera artifacts compensated for.

Figure 12:
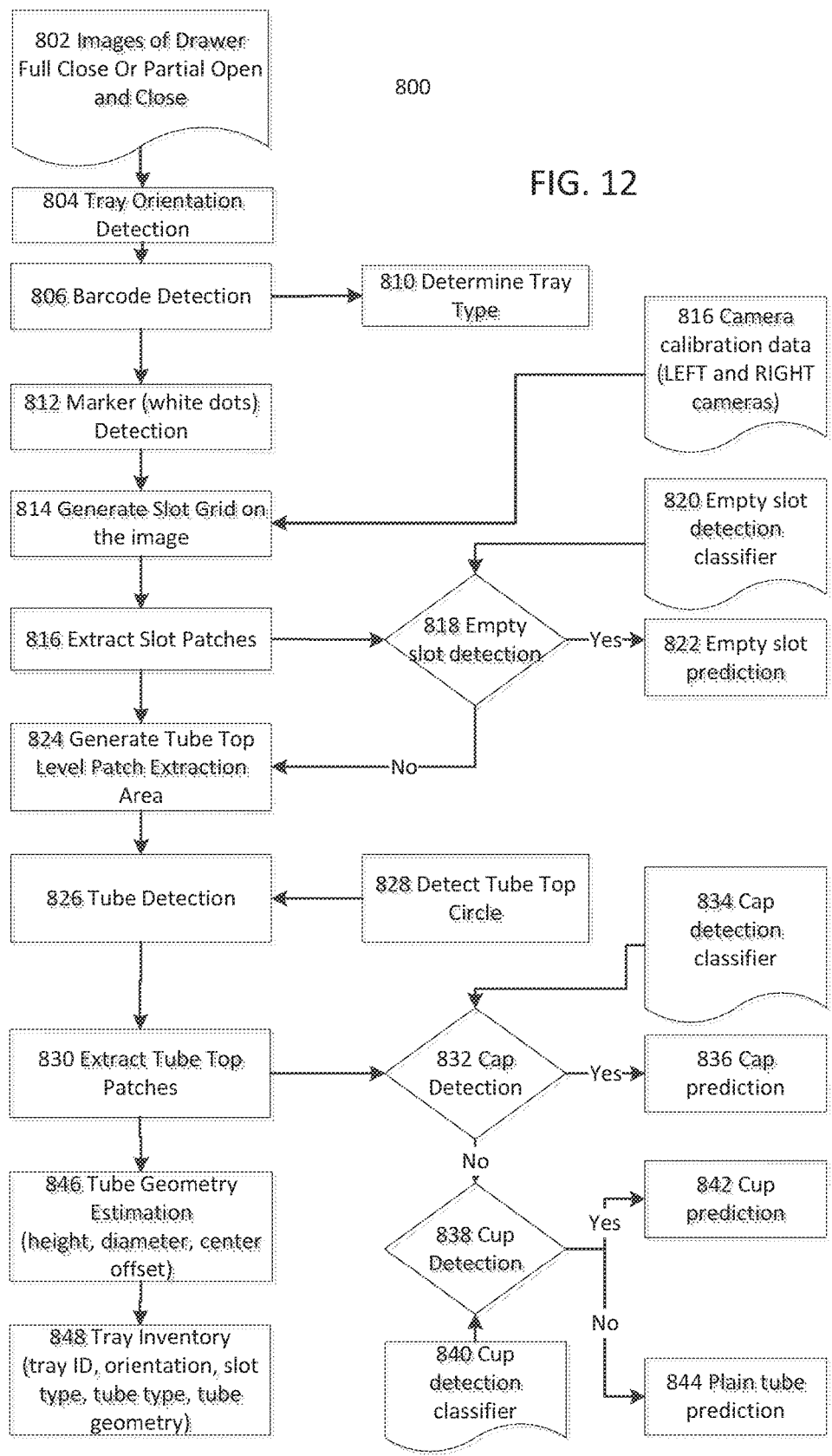
FIG. 12 is flowchart of data and processing modules used to operate a DVS for use with some embodiments.

FIG. 12 shows the exemplary software data flow 800 for operating a drawer vision system at run time to process images from a drawer vision system and characterize the contents of a sample tray. Images 802 contain images captured by the drawer vision system as a drawer is inserted. These images can include images of portions of sample trays in the drawer when the drawer is fully closed or partially open. Software module 804 detects the tray orientation of the contents of the drawer, as discussed herein. Software module 806 detects barcodes on the surface of the sample trays. This allows software to determine a tray type and/or an identity of the tray at step 810. Software module 812 provides marker detection, identifying the location of fiducial marks, such as white dots, on the surface of the tray. Software module 814 generates a slot grid onto the image based on the location of these fiducial marks, as discussed above. Module 814 utilizes camera calibration data 816 two compensate for the optical properties of the cameras that capture images containing the fiducial marks.

Software module 816 extracts image patches corresponding to slots based on the grid overlay of the images to determine the location of slots in the images. These slot image patches are provided to empty slot to detection module 818. Detection module 818 utilizes the empty slot detection classifier 820 that has been previously trained. Utilizing image patches corresponding to each tray slot and the detection classifier each 20, detection module 818 determines whether or not each slot is empty. If a slot is determined to be empty, this results in an empty slot prediction 822, allowing the slot to be classified as empty. Software module 824 generates tube top level patch extraction areas in the images to bound the search for the tops of tubes in the images. In some embodiments, module 824 only executes for each area corresponding to a non-empty slot. Software module 826 provides tube top detection for each tube top level extraction area. To complete this task, module 826 performs step 828 to detect the presence of a circle in the extraction area, which corresponds to the top of a tube.

Software module 830 extracts the tube top patches identified by module 826, allowing the image patch containing of the circle corresponding to the top of the tube to be further examined.

Software module 832 provides cap detection by examining the tube top patches provided by module 830 and utilizing the cap extraction classifiers 834 that have been previously trained. If cap detection module 832 detects a cap, this results in a prediction of the presence of a cap 836. If not, software module 838 provides tube top cup detection by analyzing the tube top patches utilizing tube top cup detection classifier 840, which may be trained as previously discussed. The result of operation of module 838 is that the tube can be identified as having a predicted cup (data structure 842) or predicted to be a plain tube (data structure 844). Software module 846 provides tube geometry estimation as previously discussed, by analyzing the image to identify a height estimation, a diameter estimation, and a center offset estimation. Software module 848 can provide aggregate analysis of the tray and tubes, identifying the trait inventory. This can include an identification of a tray ID, which may be provided by barcode detection module 806; an orientation of the tray, which may be provided by tray orientation module 804; a slot type, which may be provided by data structure 822; a tube type, which may be provided by data structures 836, 842, and 844; and tube geometry, which may be provided by tube geometry estimation module 846.

Embodiments of the present invention may be integrated with existing analyzers and automation systems. It should be appreciated that carriers may be configured in many shapes and sizes, including layouts and physical configurations suitable for use with any contemplated analyzer or instrument. For example, in some embodiments, a carrier may include multiple slots for carrying multiple samples around an automation track. One embodiment, for example, may include a physical layout of a tube-holding portion of a carrier with multiple slots in one or more transport racks. Each rack may include multiple slots (e.g., five or more slots), each slot configured to hold a tube (e.g., a sample tube).

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A method for detecting properties of sample tubes, comprising steps of:
   a) capturing a series of images of a sample tray using at least one overhead camera;
   b) receiving at a processor the series of images of the tray from the at least one overhead camera;
   c) extracting, by the processor, a plurality of image patches from each image, each image patch corresponding to a portion of each image based on features in each image;
   d) automatically determining, using the processor, from a first subset of the plurality image patches, each patch corresponding to one of a plurality of slots in the tray, whether each of a plurality of slots contains a sample tube;

e) for those plurality of slots that contain a sample tube, automatically determining, using the processor, from a second subset of the plurality image patches, each patch corresponding to the top of the sample tube, whether each sample tube has a cap; and f) for those tubes that do not have a cap, automatically determining, using the processor, from the second subset of the plurality image patches whether each sample tube has a tube-top cup or is a plain tube.

2. The method of claim 1, wherein the series of images comprises images of the tray at predetermined positions in a tray drawer.

3. The method of claim 1, wherein the processor uses a set of fiducial markers on the tray surface to determine the location of each patch corresponding to one of a plurality of slots in the tray.

4. The method of claim 1, wherein the step of automatically determining whether each of a plurality of slots contains a sample tube comprises:

a. for each slot, identifying a patch in at least one image in the series of images that corresponds to that slot based on optical marks on the tray surface; and b. determining, for each identified patch, a probability that the slot is occupied by a sample tube.

5. The method of claim 1, wherein the step of automatically determining whether each sample tube has a cap comprises:

a. for each sample tube, identifying a patch in at least one image in the series of images that corresponds to the top of the sample tube based on the detection of a circle in the at least one image; and b. determining, for each identified patch, a probability that the sample tube has a cap.

6. The method of claim 1, wherein the step of automatically determining whether each sample tube has a tube-top cup comprises:

a. for each sample tube, identifying a patch in at least one image in the series of images that corresponds to the top of the sample tube; and b. determining, for each identified patch, a probability that the sample tube has a tube-top cup.

7. The method of claim 1, further comprising the step of automatically determining, using the processor, for each sample tube, at least one of: tube type; tube height; tube diameter; tube offset; cap color; and fluid type.

8. The method of claim 1, further comprising the step of automatically identifying, using the processor, a tray type from the series of images.

9. The method of claim 1, further comprising the step of calibrating at least one camera, which is configured to capture the plurality of images, using a 3D target having a plurality of unique digital markers.

10. The method of claim 1, further comprising the step of training the processor to perform the determining steps using a random forest technique and a plurality of training images.

11. A vision system for use in an in vitro diagnostics environments comprising:

a drawer configured to receive a tray, wherein the tray comprises a plurality of slots, each configured to receive a sample tube;

at least one overhead camera configured to capture a series of images of the tray as the drawer is moved;

a processor configured to perform the following steps:

a. receiving the series of images of the tray from the at least one camera;

b. extracting a plurality of image patches from each image, each image patch corresponding to a portion of each image based on features in each image;

c. automatically determining, from a first subset of the plurality image patches, each patch corresponding to one of a plurality of slots in the tray, whether each of a plurality of slots contains a sample tube;

d. for those plurality of slots that contain a sample tube, automatically determining, from a second subset of the plurality image patches, each patch corresponding to the top of the sample tube, whether each sample tube has a cap; and e. for those tubes that do not have a cap, automatically determining, from the second subset of the plurality image patches whether each sample tube has a tube-top cup.

12. The system of claim 11, wherein the series of images comprises images of the tray at predetermined positions in the drawer.

13. The system of claim 11, wherein a set of fiducial markers on the surface of the tray to determine each patch corresponding to one of a plurality of slots in the tray.

14. The system of claim 11, wherein the step of automatically determining whether each of a plurality of slots contains a sample tube comprises:

a. for each slot, identifying a patch in at least one image in the series of images, which corresponds to that slot based on optical marks on the tray surface; and b. determining, for each identified patch, a probability that the slot is occupied by a sample tube.

15. The system of claim 11, wherein the step of automatically determining whether each sample tube has a cap comprises:

a. for each sample tube, identifying a patch in at least one image in the series of images that corresponds to the top of the sample tube based on the detection of a circle in the at least one image; and b. determining, for each identified patch, a probability that the sample tube has a cap.

16. The system of claim 11, wherein the step of automatically determining whether each sample tube has a tube-top cup comprises:

a. for each sample tube, identifying a patch in at least one image in the series of images that corresponds to the top of the sample tube; and b. determining, for each identified patch, a probability that the sample tube has a tube-top cup.

17. The system of claim 11, further comprising the step of automatically determining, using the processor, for each sample tube, at least one of: tube type; tube height; tube diameter; tube offset; cap color; and fluid type.

18. The system of claim 11, wherein the processor is configured to perform the step of automatically identifying a tray type from the series of images.

19. The system of claim 11, wherein the processor is configured to perform the step of calibrating the at least one camera using a 3D target having a plurality of unique digital markers.

20. The system of claim 11, wherein the processor is configured to perform the step of training the processor to perform the determining steps using a random forest technique and a plurality of training images.

* * * * *